United States Patent [19]

Rody et al.

[11] Patent Number: 5,070,007
[45] Date of Patent: Dec. 3, 1991

[54] COLOR PHOTOGRAPHIC MATERIALS COMPRISING PHENOLIC THIANE DERIVATIVES AS LIGHT AND THERMAL OXIDATION STABILIZERS

[75] Inventors: Jean Rody, Riehen; David G. Leppard, Marly, both of Switzerland

[73] Assignee: Ciba-Geigy AG, Basel, Switzerland

[21] Appl. No.: 651,612

[22] Filed: Feb. 6, 1991

Related U.S. Application Data

[62] Division of Ser. No. 251,082, Sep. 29, 1988, Pat. No. 5,006,665.

[30] Foreign Application Priority Data

Sep. 30, 1987 [CH] Switzerland ............... 3800/87

[51] Int. Cl.$^5$ .............. G03C 1/84; G03C 7/26; C07D 335/02
[52] U.S. Cl. ........................... 430/551; 430/17; 430/512; 430/523; 430/931
[58] Field of Search ............... 430/551, 512, 523, 17, 430/931

[56] References Cited

U.S. PATENT DOCUMENTS

| | | | |
|---|---|---|---|
| 3,935,016 | 1/1976 | Nishimura et al. | 96/74 |
| 4,297,354 | 10/1981 | Weber et al. | 424/248 |
| 4,452,884 | 6/1984 | Leppard | 430/551 |
| 4,465,765 | 8/1984 | Leppard et al. | 430/512 |
| 4,514,481 | 4/1985 | Scozzafava et al. | 430/58 |
| 4,526,864 | 7/1985 | Takada et al. | 430/551 |

FOREIGN PATENT DOCUMENTS 58-181051 10/1983 Japan.

OTHER PUBLICATIONS

Gais, Angewandte Chemie, International Edition in English, vol. 16, No. 3, (Mar. 1977), pp. 196–197.
Matsuyama et al., Journal of Organic Chemistry, vol. 52, No. 9 (May 1987), pp. 1703–1710.

*Primary Examiner*—Charles L. Bowers, Jr.
*Assistant Examiner*—Patrick A. Doody
*Attorney, Agent, or Firm*—Wenderoth, Lind & Ponack

[57] ABSTRACT

Phenolic thiane derivatives of the formula I or II

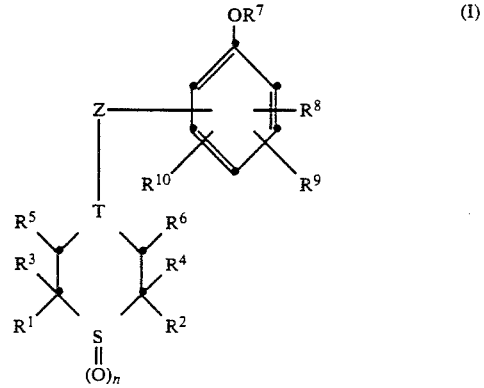

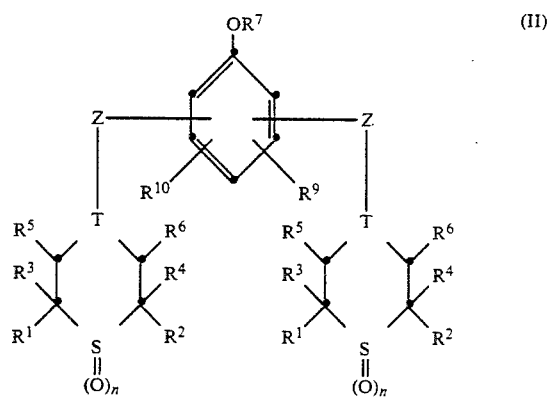

in which n is 0, 1 or 2 and $R^1$, $R^2$, $R^3$, $R^4$, $R^5$, $R^6$, $R^7$, $R^8$, $R^9$, $R^{10}$, T and Z are as defined in claim 1, are effective stabilizers for color photography recording materials, in particular for the yellow layer. They act not only as light stabilizers but also as stabilizers against thermal oxidation.

10 Claims, No Drawings

COLOR PHOTOGRAPHIC MATERIALS COMPRISING PHENOLIC THIANE DERIVATIVES AS LIGHT AND THERMAL OXIDATION STABILIZERS

This application is a division of application Ser. No. 251,082 filed Sep. 29, 1988 now U.S. Pat. No. 5,006,665.

The present invention relates to novel phenolic derivatives of tetrahydrothiopyran (thiane) and their use as stabilizers for colour photography recording materials.

These are compounds of the formula I or II

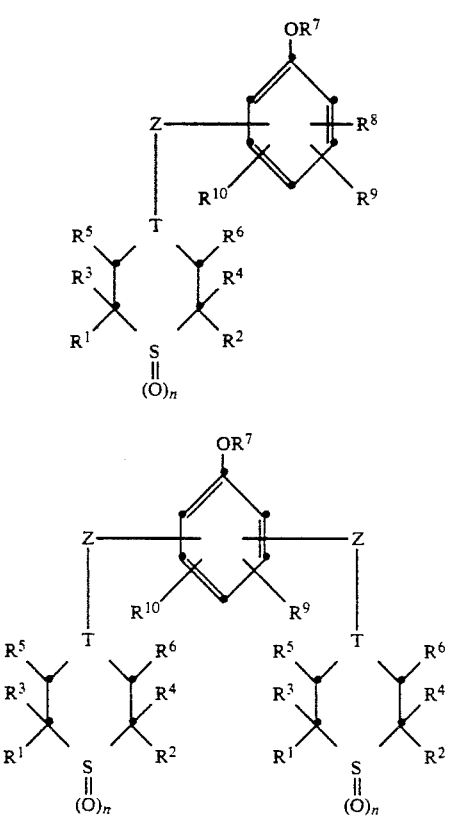

in which n is 0, 1 or 2, $R^1$ and $R^2$ independently of one another are hydrogen or methyl, $R^3$ and $R^4$ independently of one another are hydrogen, $C_1$–$C_4$alkyl, phenyl, thienyl or phenyl which is substituted by 1 or 2 $C_1$–$C_8$alkyl groups, cyclohexyl, phenyl, $C_7$–$C_9$phenylalkyl, hydroxyl, $C_1$–$C_{18}$alkoxy or halogen, $R^5$ and $R^6$ independently of one another are hydrogen, $C_1$–$C_4$alkyl, phenyl, —COO($C_1$–$C_{18}$ alkyl), —CO—CH$_3$ or —CO—phenyl, $R^7$ is hydrogen, $C_1$–$C_8$alkyl or one of the groups —CO—$R^{11}$, —CO—COO($C_1$–$C_4$alkyl), —SO$_2$—$R^{12}$, —CON($R^{13}$)($R^{14}$), —Si($R^{15}$)($R^{16}$)($R^{17}$) or

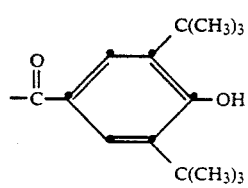

$R^8$ and $R^9$ independently of one another are hydrogen, $C_1$–$C_{12}$alkyl, $C_7$–$C_9$phenylalkyl, $C_5$–$C_8$cycloalkyl or phenyl, $R^{10}$ is hydrogen, —O$R^7$ or a group of the formula III

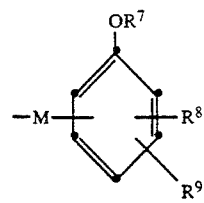

in which M is a direct bond, —O—, —S—, —S—S—, —CH$_2$—, —CH($C_1$–$C_8$alkyl)— or —C(CH$_3$)$_2$—, $R^{11}$ is $C_1$–$C_{20}$alkyl, $C_3$–$C_{20}$alkenyl, $C_5$–$C_{12}$cycloalkyl, $C_7$–$C_{13}$phenylalkyl or $C_6$–$C_{10}$aryl, $R^{12}$ is $C_1$–$C_{12}$alkyl, $C_6$–$C_{10}$aryl or $C_7$–$C_{24}$alkylaryl, $R^{13}$ is hydrogen, $C_1$–$C_{12}$alkyl or cyclohexyl, $R^{14}$ is $C_1$–$C_{12}$alkyl, $C_6$–$C_{10}$aryl, $C_1$–$C_{12}$alkylsubstituted $C_6$–$C_{10}$aryl or cyclohexyl, or $R^{13}$ and $R^{14}$, together with the N atom, form a 5- or 6-membered saturated heterocyclic ring, $R^{15}$, $R^{16}$ and $R^{17}$ independently of one another are $C_1$–$C_{12}$alkyl, $C_3$–$C_{12}$alkenyl, phenyl, cyclohexyl or benzyl, T is a trivalent group which completes the ring to give a thiane ring and is one of the following groups:

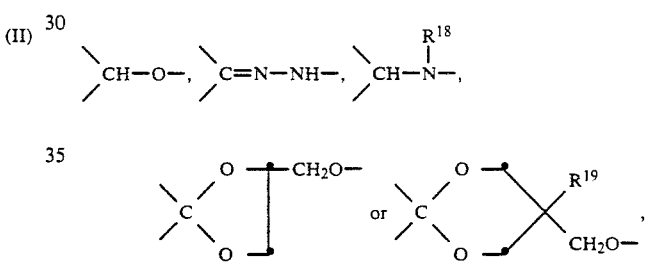

in which $R^{18}$ is hydrogen, $C_1$–$C_{12}$alkyl, benzyl, cyclohexyl or phenyl and $R^{19}$ is hydrogen or $C_1$–$C_4$alkyl, Z is a divalent bonding member between T and the phenol radical and is one of the following groups:

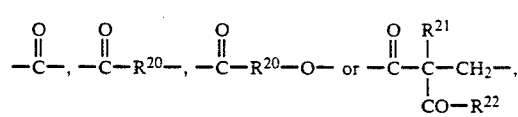

the carbonyl group of which is bonded to T and in which $R^{20}$ is $C_1$–$C_{14}$alkylene, $R^{21}$ is hydrogen, $C_1$–$C_{12}$alkyl, phenyl, $C_7$–$C_9$phenylalkyl or a group of the formula IV

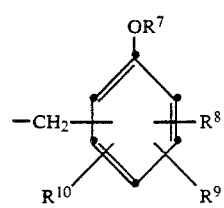

and $R^{22}$ is a group —O($C_1$–$C_4$alkyl) or a group of formula V

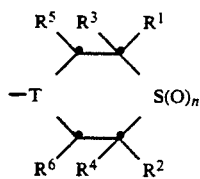

Where these substituents are alkyl or alkylene, these groups can be unbranched or branched. If $R^{13}$ and $R^{14}$, together with the N atom, form a saturated heterocyclic ring, they can additionally also contain an O, N or S atom. Examples are a pyrrolidine, piperidine, morpholine or piperazine ring, which can be substituted by one or two $C_1$-$C_4$alkyl groups.

Preferred compounds of the formula I or II are those in which n is 0 or 2, $R^1$ and $R^2$ are hydrogen or methyl, $R^3$ and $R^4$ independently of one another are methyl, phenyl, thienyl or phenyl which is substituted by one or two $C_1$-$C_4$alkyl groups, cyclohexyl, hydroxyl, $C_1$-$C_4$alkoxy or chlorine, $R^5$ and $R^6$ independently of one another are hydrogen, —COO($C_1$-$C_4$alkyl) or —COCH$_3$, $R^7$ is hydrogen or a group —CO—$R^{11}$, —CO—COO($C_1$-$C_4$-alkyl), —Si(CH$_3$)$_3$ or

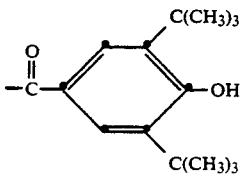

$R^8$ and $R^9$ independently of one another are $C_1$-$C_8$alkyl, $C_7$-$C_9$phenylalkyl, cyclohexyl or phenyl, $R^{10}$ is hydrogen, —OR$^7$ or a group of the formula III, in which M is —S—, —CH$_2$—, —CH($C_1$-$C_4$alkyl) or —C(CH$_3$)$_2$—, $R^{11}$ is $C_1$-$C_{12}$alkyl or phenyl, T is one of the following trivalent groups:

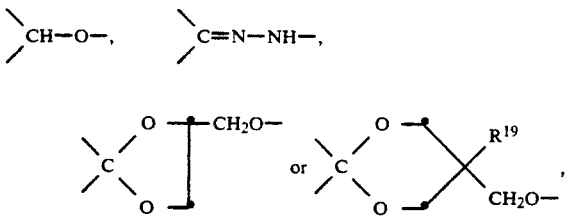

which $R^{19}$ is $C_1$-$C_4$alkyl, and Z is one of the following divalent groups:

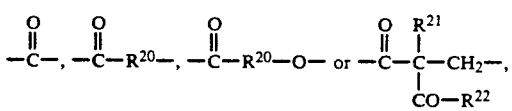

the carbonyl group of which is bonded to T and in which $R^{20}$ is $C_1$-$C_{14}$alkylene, $R^{21}$ is $C_1$-$C_8$alkyl, benzyl or a group of the formula IV and $R^{22}$ is a group —O($C_1$-$C_4$alkyl) or a group of the formula V.

Particularly preferred compounds of the formula I and II are those in which n is 0 or 2, $R^1$ and $R^2$ are hydrogen or methyl, $R^3$ and $R^4$ are methyl, phenyl, thienyl or phenyl which is substituted by $C_1$-$C_4$alkyl, $C_1$-$C_4$alkoxy, hydroxyl or chlorine, $R^5$ and $R^6$ are hydrogen, $R^7$ is hydrogen or a group

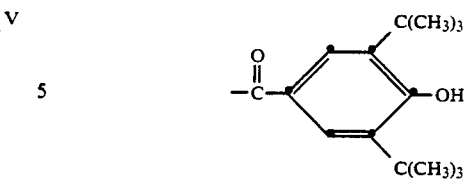

$R^8$ and $R^9$ independently of one another are hydrogen, $C_1$-$C_4$alkyl, cyclohexyl or phenyl, $R^{10}$ is hydrogen, T is one of the following trivalent groups:

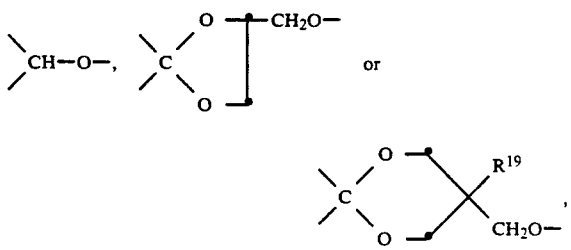

in which $R^{19}$ is $C_1$-$C_4$alkyl, and Z is one of the following divalent groups:

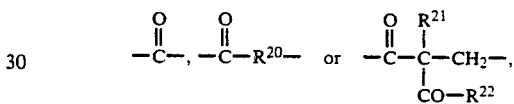

the carbonyl group of which is bonded to T and in which $R^{20}$ is $C_1$-$C_8$alkylene, $R^{21}$ is $C_1$-$C_8$alkyl, benzyl or a group of the formula IV and $R^{22}$ is —O($C_1$-$C_4$alkyl) or a group of the formula V.

Preferred compounds of the formula I and II are those in which $R^1$, $R^2$, $R^5$ and $R^6$ are hydrogen.

The sulfur in the thiane ring can be present as sulfide, sulfoxide or sulfone sulfur, depending on whether n is zero, 1 or 2. n is preferably zero or 2, and in particular zero.

Compared with the compounds of the formula II, the compounds of the formula I are preferred.

Examples of compounds of the formula I are:
1) 4-(3,5-di-tert-butyl-4-hydroxybenzoyloxy)-thiane
2) 4-[3-(3,5-di-tert-butyl-4-hydroxyphenyl)-propionyloxy]-thiane
3) 4-(3,5-di-tert-butyl-4-hydroxybenzoyloxy)-2,2,6,6-tetramethylthiane
4) 4-[3-(3,5-di-tert-butyl-4-hydroxyphenyl)-propionyloxy]-2,2,6,6-tetramethylthiane
5) 4-[3-(3,5-di-tert-butyl-4-hydroxyphenyl)-propionyloxy]-1-oxo-2,2,6,6-tetramethylthiane
6) 4-[3-(3,5-di-tert-butyl-4-hydroxyphenyl)-propionyloxy]-1,1-dioxo-2,2,6,6-tetramethylthiane
7) 4-[5,5-dimethyl-5-(2-hydroxy-5-methoxyphenyl)-valerianyloxy]-2,2,6,6-tetramethylthiane
8) 4-[α,α-bis(3,5-di-tert-butyl-4-hydroxybenzyl)-α-methoxycarbonylacetoxy]-2,2,6,6-tetramethylthiane
9) 4-(3,5-di-tert-butyl-4-hydroxybenzoyloxy)-2,6-diphenylthiane
10) 4-[3-(3,5-di-tert-butyl-4-hydroxyphenyl)-propionyloxy]-2,6-diphenylthiane
11) N-[3-(3,5-di-tert-butyl-4-hydroxyphenyl)-propionyloxy]-2,6-diphenylthiane-4-hydrazone
12) 4-[3-(3,5-di-tert-butyl-4-hydroxyphenyl)-propionyloxy]-1,1-dioxo-2,6-diphenylthiane 13) 4-[3-(3-methyl-4-hydroxy-5-tert-butylphenyl)-propionyloxy]-1,1-dioxo-2,6-diphenylthiane
14) N-[3-(3-methyl-4-hydroxyphenyl-5-tert-butylphenyl)-propionyloxy]-2,6-diphenylthiane-4-hydrazone
15) 1,4-dioxa-3-(3,5-di-tert-butyl-4-hydroxybenzoyloxymethyl)-7,9-diphenyl-8-tetra[4.5]spirodecane
16) 1,4-dioxa-3-[β-(3,5-di-tert-butyl-4-hydroxyphenyl)-propionyloxymethyl]-7,9-diphenyl-8-thia[4.5]spirodecane
17) 1,4-dioxa 3-[β-(3-methyl-4-hydroxy-5-tert-butylphenyl)-propionyloxymethyl]-7,9-diphenyl-8-thia[4.5]spirodecane
18) 1,5-dioxa-3-ethyl-(3,5-di-tert-butyl-4-hydroxybenzoyloxymethyl)-8,10-diphenyl-9-thia[5.5]spiroundecane
19) 1,5-dioxa-3-ethyl-3-[β-(3,5-di-tert-butyl-4-hydroxyphenyl)-propionyloxymethyl]-8,10-diphenyl-9-thia-[5.5]spiroundecane
20) 1,5-dioxa-3-ethyl-3-[β-(3-methyl-4-hydroxy-5-tert-butylphenyl)propionyloxymethyl]-8,10-diphenyl-9-thia[5.5]spiroundecane
21) 1,5-dioxa-3-ethyl-3-[β-(3,5-di-tert-butyl-4-hydroxyphenyl)-propionyloxymethyl]-8,10-diphenyl-9-thia-9,9-dioxo[5.5]spiroundecane
22) 1,5-dioxa-3-ethyl-3-[β-(3-methyl-4-hydroxy-5-tert-butylphenyl)propionyloxymethyl]-8,10-diphenyl-9-thia-9,9-dioxo[5.5]spiroundecane
23) 1,5-dioxa-3-ethyl-3-[α-(3,5-di-tert-butyl-4-hydroxyphenoxy)-acetyloxymethyl]-8,10-diphenyl-9-thia[5.-5]undecane
24) 1,5-dioxa-3-ethyl-3-[β-(3-methyl-4-methyloxalyloxy-5-tert-butylphenyl)-propionyloxymethyl]-8,10-diphenyl-9-thia[5.5]undecane
25) 1,5-dioxa-3-ethyl-3-[β-(3-methyl-4-trimethylsiloxy-5-tert-butyl)propionyloxymethyl]-8,10-diphenyl-9-thia[5.5]undecane
26) 1,5-dioxa-3-ethyl-3-[5,5-dimethyl-5-(2-hydroxy-5-methoxyphenyl)valeryloxymethyl]-8,10-diphenyl-9-thia[5.5]undecane
27) 1,5-dioxa-3-ethyl-3-[2-(3-tert-butyl-4-hydroxyphenyl)-tetradecanoyloxymethyl]-8,10-diphenyl-9-thia[5.5]undecane
28) 1,5-dioxa-3-ethyl-3-[5,5-dimethyl-5-(2-hydroxy-3,5-dimethylphenyl)valeryloxymethyl]-8,10-diphenyl-9-thia[5.5]undecane
29) 1,5-dioxa-3-ethyl-3-[5,5-dimethyl-5-(3-methyl-4-hydroxyphenyl)valeryloxymethyl]-8,10-diphenyl-9-thia[5.5]undecane
30) 1,5-dioxa-3-ethyl-3-[5,5-dimethyl-5-(2-hydroxy-5-tert-butylphenyl)valeryloxymethyl]-8,10-diphenyl-9-thia[5.5]undecane
31) 1,5-dioxa-3-ethyl-3-[5,5-dimethyl-5-(3,5-dimethyl-4-hydroxypheynl)-valeryloxymethyl]-8,10-diphenyl-9-thia[5.5]undecane
32) 1,5-dioxa-3-ethyl-3-[5,5-dimethyl-5-(2-methyloxalyloxy-3,5-dimethyl)valeryloxymethyl]-8,10-diphenyl-9-thia[5.5]undecane
33) 1,5-dioxa-3-ethyl-3-[5,5-dimethyl-5-(3,5-di-tert-butyl-4-hydroxyphenyl)-valeryloxymethyl]-8,10-diphenyl-9-thia[5.5]undecane
34) 4-(3,5-di-tert-butyl-4-hydroxybenzoyloxy)-2,6-di(4-chlorophenyl)thiane
35) 4-[3-(3,5-di-tert-butyl-4-hydroxyphenyl)-propionyloxy]-2,6-di(4-chlorophenyl)-thiane
36) 4-[3-(3-methyl-4-hydroxy-5-tert-butylphenyl)-propionyloxy]-2,6-di(4-chlorophenyl)-thiane
37) 4-[3-(3,5-di-tert-butyl-4-hydroxyphenyl)-propionyloxy]-2,6-di(4-methoxyphenyl)-thiane
38) 1,5-dioxa-3-ethyl-3-(3,5-di-tert-butyl-4-hydroxybenzoyloxymethyl-8,10-di(4-chlorophenyl)-9-thia[5.-5]undecane
39) 1,5-dioxa-3-ethyl-3-[3-(3,5-di-tert-butyl-4-hydroxyphenyl)-propionyloxymethyl]-8,10-di(4-chlorophenyl)-9-thia[5.5]undecane
40) 1,5-dioxa-3-ethyl-3-[3-(3-methyl-4-hydroxy-5-tert-butylphenyl)propionyloxymethyl]-propionyloxymethyl[-8,10-di(4-chlorophenyl)-9-thia[5.5]undecane
41) 1,5-dioxa-3-ethyl-3-[3-(3-methyl-4-hydroxy-5-tert-butylphenyl)propionyloxymethyl]-8,10-di(3-methyl-4-hydroxy-5-tert-butylphenyl)-9-thia[5.5]undecane
42) 4-(3,5-di-tert-butyl-4-hydroxybenzoyloxy)-2,6-di(2-thienyl)-thiane
43) 4-[3-(3,5-di-tert-butyl-4-hydroxyphenyl)-propionyloxy]-2,6-di(2-thienyl)-thiane
44) 4-[3-(3-methyl-4-hydroxy-5-tert-butylphenyl)-propionyloxy]-2,6-di(2-thienyl)-thiane
45) 1,5-dioxa-3-ethyl-3-[β-(3-tert-butyl-4-hydroxyphenyl)-propionyloxymethyl]-8,10-diphenyl-9-thia[5.5]spiroundecane
46) 1,5-dioxa-3-ethyl-3-[β-(3-methyl-5-tert-butyl-4-[methyloxalyloxy]phenyl)-propionyloxymethyl]-8,10-diphenyl-9-thia[5.5]spiroundecane
47) 1,5-dioxa-3-ethyl-3-[β-(3-methyl-5-tert-butyl-4-[trimethylsiloxy]phenyl)-propionyloxymethyl]-8,10-diphenyl-9-thia[5.5]spiroundecane
48) N-[β-(3-methyl-4-hydroxy-5-tert-butylphenyl)-propionylamido]-2,6-diphenyl-4-iminothiane
49) N-[β-(3,5-di-tert-butyl-4-hydroxyphenyl)-propionylamido]-2,6-di-phenyl-4-iminothiane
50) methyl 2,2,6,6-tetramethylthian-4-yl bis-(3,5-di-tert-butyl-4-hydroxybenzyl)-malonate
51) di(2,2,6,6-tetramethylthian-4-yl) bis-(3,5-di-tert-butyl-4-hydroxybenzyl)malonate
52) the compound of the formula

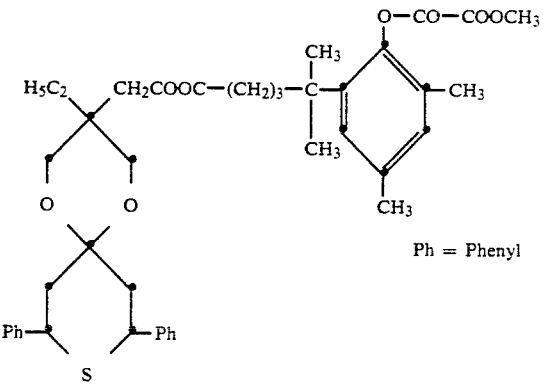

Ph = Phenyl

Examples of compounds of the formula II are the compounds of the following formulae:

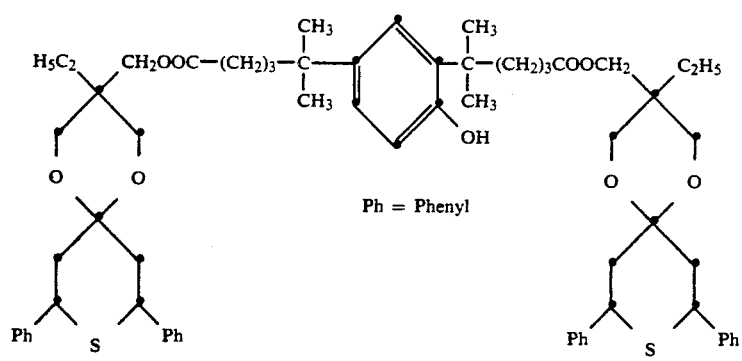
53)
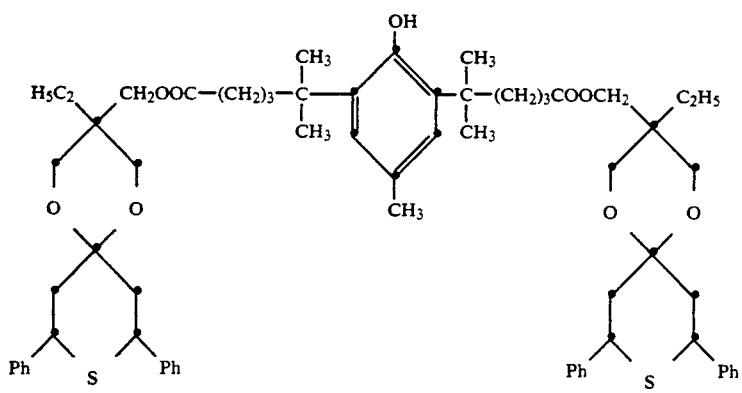
54)
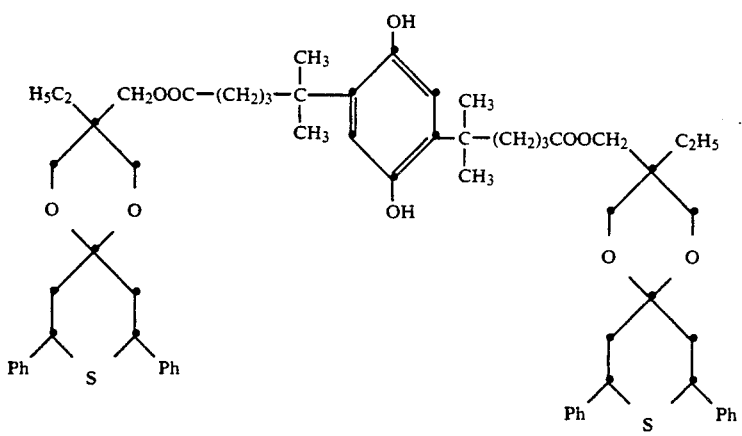
55)
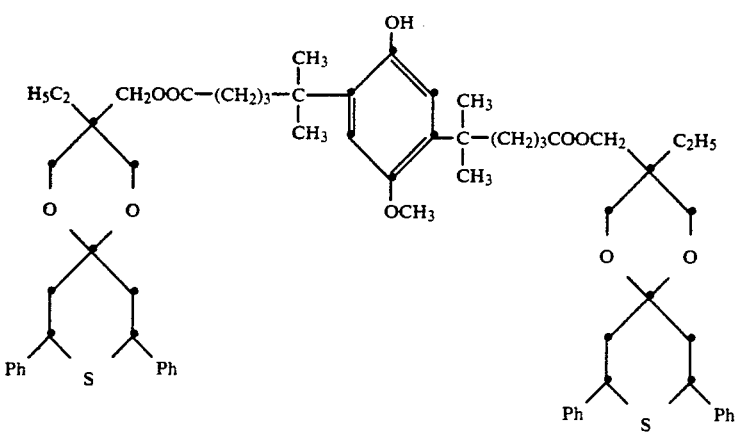
56)

-continued

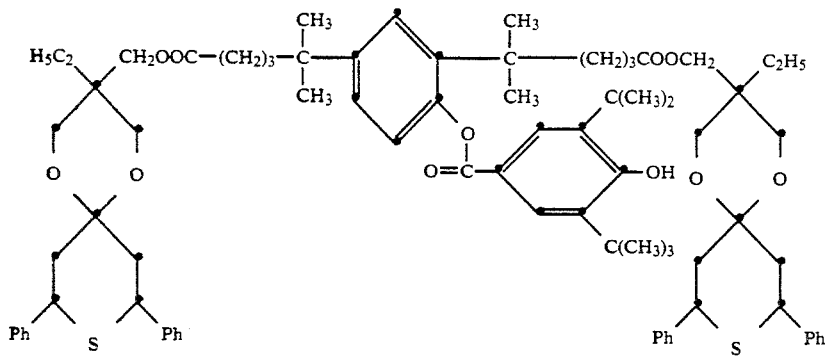

57)

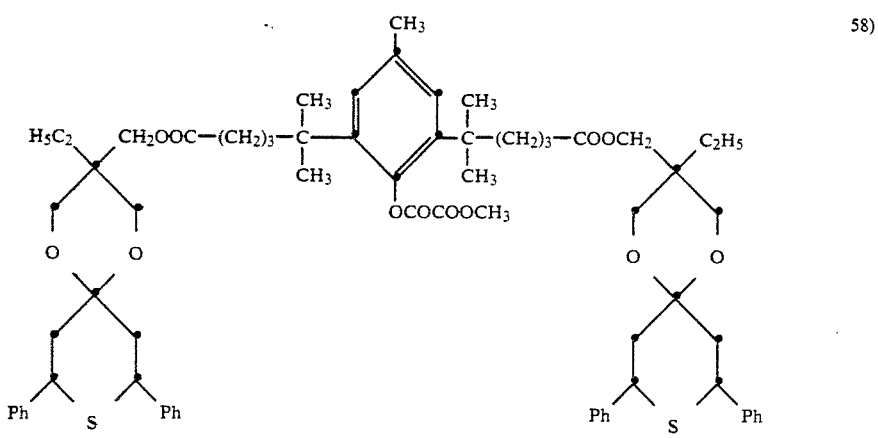

58)

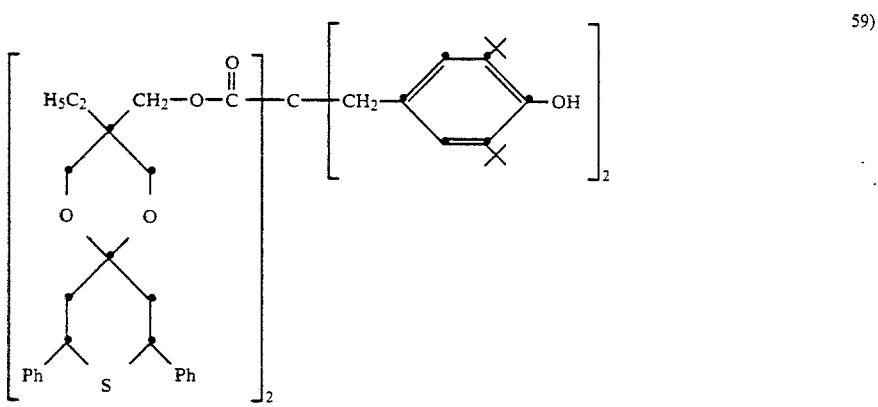

59)

The compounds of the formula I or II can be prepared by reacting a phenolic carboxylic acid or derivative thereof VI with an OH- or NH-functional thiane derivative VII:

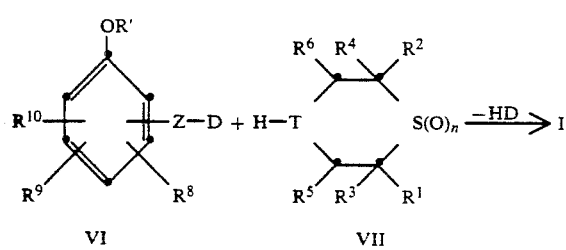

$D = OH$, $O(C_1-C_4 alkyl)$ or $Cl$

Compounds of the formula II are prepared analogously by reacting a phenolic dicarboxylic acid or derivative thereof VIII with 2 equivalents of VII:

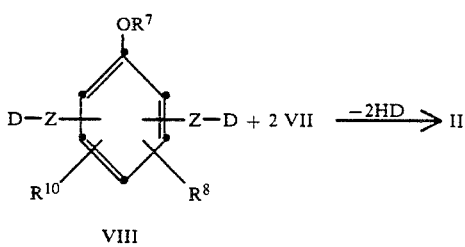

VIII

If VII is an OH-functional thiane derivative, the reaction is carried out under the customary conditions of esterification (D=OH), transesterification (D=O-alkyl) or O-acylation (D=Cl). The esterification is preferably carried out under acid catalysis and the transesterification under basic catalysis. The O-acylation by means of the carboxylic acid chloride is preferably carried out in the presence of equivalent amounts of a base.

The phenolic carboxylic acids and their derivatives of the formula VI and VIII are known compounds or can be prepared by methods which are known per se.

The functional thianes of the formula VII are in some cases known compounds or can be prepared by processes analogous to known processes. Thus, compounds of the formula VII in which >T—H is a group >CH—OH can be obtained by reduction of the corresponding ketones with borohydrides in accordance with the method of J. Klein, H. Stollar/Tetrahedron 30, 2541 (1974) or K. Ramalingam et al./J. Org. Chem. 44 477 (1979). Compounds of the formula VII in which >T—H is a group >—CH—NH$_2$ can be prepared by reduction of the oximes >C=NOH with LiAlH$_4$ in accordance with the method of P.K. Subramanian et al./J. Org. Chem. 46, 4376 (1981). Compounds of the formula VII in which >T—H is a group >C=N—NH$_2$ are obtained by reaction of the corresponding thianones with hydrazine. Compounds of the formula VII in which T—H is a group

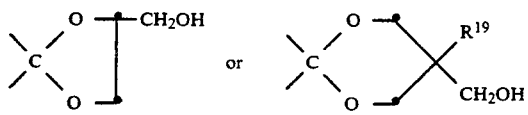

can be obtained by ketalization of the corresponding thianones with glycerol or with a polyol of the formula R$^{19}$—C(CH$_2$OH)$_3$.

The cyclic sulfoxides and sulfones of the formula I or II in which n is 1 or 2 can be obtained from the thiane derivatives where n=0 by oxidation, such as is described, for example, by J. Klein, H. Stollar/Tetrahedron 30, 2541 (1974) and P.K. Subramanian et al./J. Org. Chem. 46, 4376 (1981).

Compounds of the formula I in which T is a group >C=N—NH— can also be prepared by reaction of a thianone IX with a hydrazide of a phenolic carboxylic acid X:

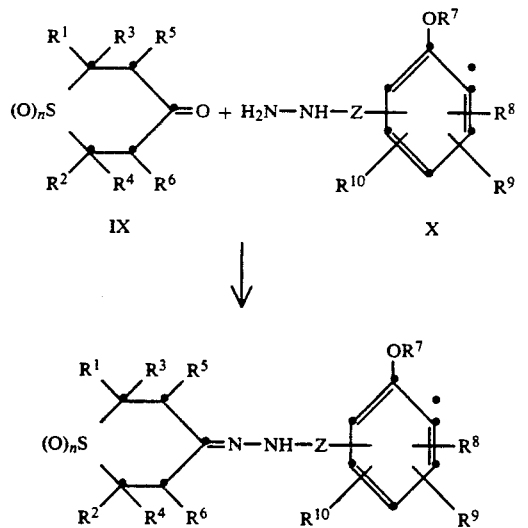

The compounds of the formula I or II can be used as stabilizers for colour photography recording materials. These materials are predominantly papers or films which contain three photosensitive layers, the yellow layer, the magenta layer and the cyan layer. These layers are gelatin layers which contain at least one silver halide and one dye coupler and can also contain other additives. The compounds of the formula I or II are added to such a gelatin layer. For this, they are dissolved in an organic solvent or solvent mixture and the solution is emulsified in a gelatin solution, which is then added to the photographic gelatin layer during preparation thereof. The solvent used is preferably a mixture of a low-boiling and a high-boiling solvent and the low-boiling solvent is removed during the emulsification.

The stabilizer solution can be dispersed in the gelatin solution, for example, in a colloid mill or in a homogenizer or with the aid of ultrasound. Surface-active agents (emulsifiers) can also be added here. A fine dispersion is a prerequisite for homogeneous distribution of the stabilizers in the photographic layer.

The compounds of the formula I or II stabilize both the colour couplers and the photographic dyes formed after exposure and development from the effect of light. They prevent or delay the bleaching or change in colour of the photographic dyes by the action of light. They do not react with the customary dye couplers and do not impede the photographic process of colour formation.

Phenolic compounds have already been proposed as stabilizers for colour photography materials, thus, for example, in EP-A-82,817, EP-A-103,540, U.S. Pat. No. 3,935,016 or EP-A-113,124. Such stabilizers have led to a considerable increase in the light-fastness of colour photographs, but there is continued interest in an improvement in the stabilization.

The stabilizers of the formula I or II are expediently added in an amount of up to 1 g/m$^2$ per colour layer, preferably 10 to 300 mg/m$^2$. They can be added to one, two or all three colour silver layers. The addition to the yellow layer is of particular importance. The layers contain the sensitized silver halide and the respective colour coupler. The layers can also contain further stabilizers and/or other additives.

The yellow couplers are preferably compounds of the formula XI

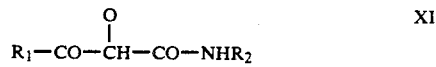

in which R$_1$ is alkyl or aryl, R$_2$ is aryl and Q is hydrogen or a group which can be split off by reaction with the oxidized developer.

A group of yellow couplers comprises those compounds of the formula XI in which R$_1$ is tert-butyl and R$_2$ is a group of the formula

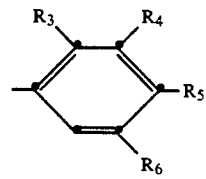

in which R$_3$ is hydrogen, halogen, alkyl or alkoxy and R$_4$, R$_5$ and R$_6$ are hydrogen, halogen, alkyl, alkenyl, alkoxy, aryl, carboxyl, alkoxycarbonyl, a carbamoyl group, a sulfone or sulfamoyl group or an alkylsulfonamido group, acylamino group, ureido group or amino group.

Preferably, $R_3$ is chlorine, $R_4$ and $R_5$ are hydrogen and $R_6$ is an acylamino group. These also include the compounds of the formula

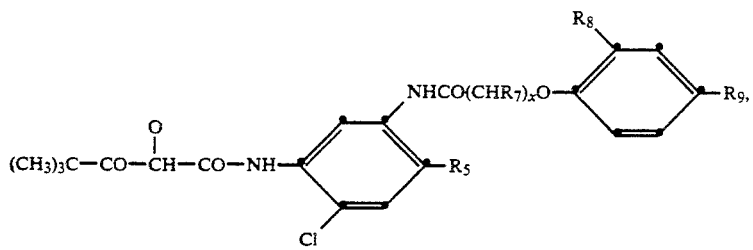

in which x is 0–4, $R_7$ is hydrogen or alkyl and $R_8$ and $R_9$ are alkyl.

Another group of yellow couplers corresponds to the formula XII

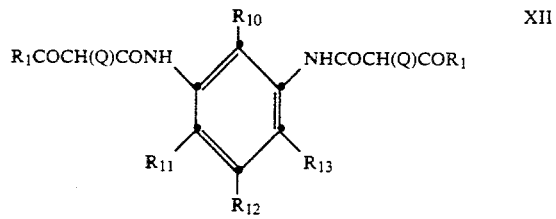

in which $R_{10}$ is hydrogen, halogen or alkoxy, $R_{11}$, $R_{12}$ and $R_{13}$ are hydrogen, halogen, alkyl, alkenyl, alkoxy, aryl, carboxyl, alkoxycarbonyl, a carbamoyl group or a sulfone group, sulfamoyl group, sulfonamido group, acylamino group, ureido group or amino group and $R_1$ and Q are as defined above.

These include compounds of the formula XII in which $R_1$ is tert-butyl, $R_{10}$ is chlorine, $R_{11}$ and $R_{13}$ are hydrogen and $R_{12}$ is alkoxycarbonyl.

In the compounds of the formula XI and XII, the leaving group Q can be hydrogen, or is a heterocyclic group

in which $R_{14}$ is an organic divalent group which completes the ring to give a 4- to 7-membered ring, or Q is a group $-OR_{15}$, in which $R_{15}$ is alkyl, aryl, acyl or a heterocyclic radical.

Typical examples of customary yellow couplers are the compounds of the following formulae:

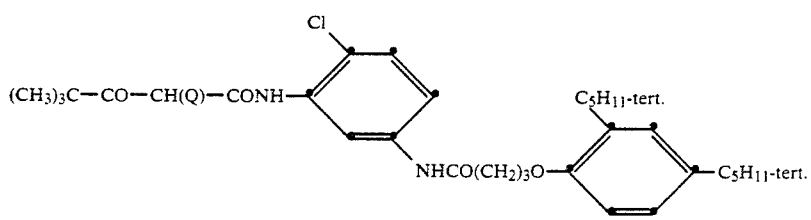

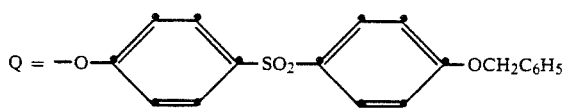

a)

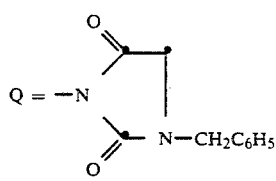

b)

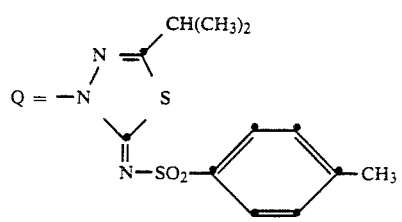

c)

-continued

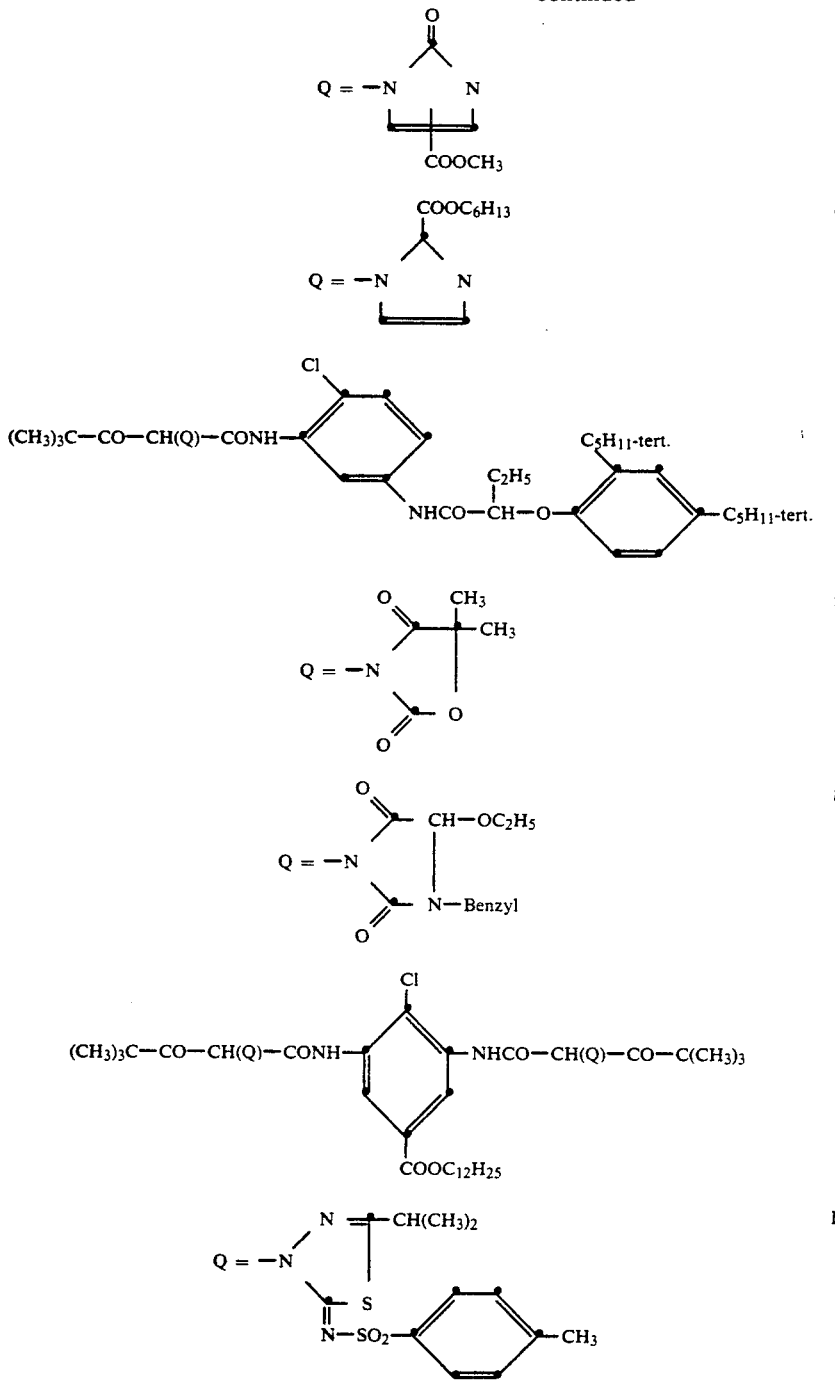

Further examples of yellow couplers are to be found in U.S. Pat. Nos. 2,407,210, 2,778,658, 2,875,057, 2,908,513, 2,908,573, 3,227,155, 3,227,550, 2,253,924, 3,265,506, 3,277,155, 3,408,194, 3,341,331, 3,369,895, 3,384,657, 3,415,652, 3,447,928, 3,551,155, 3,582,322, 3,725,072, 3,891,445, 3,933,501, 4,115,121, 4,401,752, and 4,022,620, in DE-A-1,547,868, 2,057,941, 2,162,899, 2,163,813, 2,213,461, 2,219,917, 2,261,361, 2,261,362, 2,263,875, 2,329,587, 2,414,006 and 2,422,812 and in GB-A-1,425,020 and 1,077,874.

The yellow couplers are usually employed in an amount of 0.05-2 mol and preferably 0.1-1 mol per mol of silver halide.

Magenta couplers can be, for example, simple 1-aryl-5-pyrazolones or pyrazole derivatives condensed with 5-membered hetero rings, for example imidazopyrazoles, pyrazolopyrazoles, pyrazolotriazoles or pyrazolotetrazoles.

One group of magenta couplers comprises 5-pyrazolones of the formula XIII

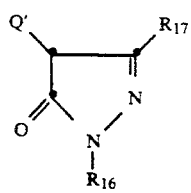

such as are described in British Patent Specification 2,003,473. In this formula, $R_{16}$ is hydrogen, alkyl, aryl, alkenyl or a heterocyclic group. $R_{17}$ is hydrogen, alkyl, aryl, a heterocyclic group or an ester group, alkoxy group, alkylthio group, carboxyl group, arylamino group, acylamino group, (thio)-urea group, (thio)-carbamoyl group, guanidino group or sulfonamido group.

Preferably, $R_{17}$ is a group

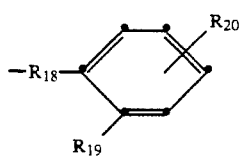

in which $R_{18}$ is imino, acylamino or ureido, $R_{19}$ is hydrogen, halogen, alkyl or alkoxy and $R_{20}$ is hydrogen, alkyl, acylamino, carbamoyl, sulfamoyl, sulfonamido, alkoxycarbonyl, acyloxy or a urethane group.

If Q' is hydrogen, the magenta coupler is tetraequivalent with respect to the silver halide.

Typical examples of this type of magenta couplers are compounds of the formula

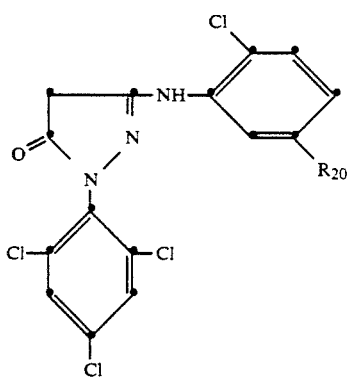

in which $R_{20}$ as defined above.

Further examples of such tetraequivalent magenta couplers are to be found in U.S. Pat. Nos. 2,983,608, 3,061,432, 3,062,653, 3,127,269, 3,152,896, 3,311,476, 3,419,391, 3,519,429, 3,558,319, 3,582,322, 3,615,506, 3,684,514, 3,834,908, 3,888,680, 3,891,445, 3,907,571, 3,928,044, 3,930,861, 3,930,866 and 3,933,500.

If Q' in formula XIII is not hydrogen but is a group which is eliminated in the reaction with the oxidized developer, the compound is a diequivalent magenta coupler. Q' can in this case be, for example, halogen or a group bonded to the pyrazole ring via O, S or N. Such diequivalent couplers give a higher colour density and are more reactive towards the oxidized developer than the corresponding tetraequivalent magenta couplers.

Examples of diequivalent magenta couplers are described in U.S. Pat. Nos. 3,006,579, 3,419,391, 3,311,476, 3,432,521, 3,214,437, 4,032,346, 3,701,783, 4,351,897 and 3,227,554, EP-A-133,503, DE-A-2,944,601 and JP-A- 78/34044, 74/53435, 74/53436, 75/53372 and 75/122,935.

2 pyrazolone rings can be linked via a divalent Q' and so-called biscouplers are then obtained. Such compounds are described, for example, in U.S. Pat. No. 2,632,702, U.S. Pat. No. 2,618,864, GB-A-968,461, GB-A-786,859 and JP-A-76/37646, 59/4086, 69/16110, 69/26589, 74/37854 and 74/29638. Y is preferably an O-alkoxyarylthio group.

As mentioned above, pyrazoles fused to 5-membered heterocyclic rings —so-called pyrazoloazoles—can also be used as magenta couplers Their advantage over simple pyrazoles is that they have colours with a greater formalin resistance and purer absorption spectra.

They can be represented by the general formula XIV

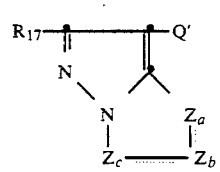

in which $Z_a$, $Z_b$ and $Z_c$ are the radicals to complete a 5-membered ring, which can contain up to 4 nitrogen atoms. The compounds can accordingly be pyrazolo-imidazoles, pyrazolo-pyrazoles, pyrazolo-triazoles or pyrazolo-tetrazoles. $R_{17}$ and Q' are as defined in formula XIII.

Pyrazolo-tetrazoles are described in JP-A-85/33552; pyrazolo-pyrazoles are described in JP-A-85/43,695; pyrazolo-imidazoles are described in JP-A-85/35732, JP-A-86/18949 and U.S. Pat. No. 4,500,630; pyrazolo-triazoles are described in JP-A-85/186,567, JP-A-86/47957, JP-A-85/215,687, JP-A-85/197,688, JP-A-85/172,982, EP-A-119,860, EP-A-173,256, EP-A-178,789, EP-A-178,788 and in Research Disclosure 84/24,624.

Further pyrazoloazole magenta couplers are described in: JP-A-86/28,947, JP-A-85/140,241, JP-A-85/262,160, JP-A-85/213,937, EP-A-177,765, EP-A-176,804, EP-A-170,164, EP-A-164,130, EP-A-178,794, DE-A-3,516,996, DE-A-3,508,766 and Research Disclosure 81/20919, 84/24531 and 85/25758.

Cyan couplers can be, for example, derivatives of phenol, of 1-naphthol or of pyrazoloquinazolone. Structures of the formula XV

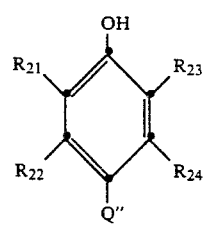

in which $R_{21}$, $R_{22}$, $R_{23}$ and $R_{24}$ hydrogen, halogen, alkyl, carbamoyl, amido, sulfonamido, phosphoramido or ureido, are preferred. $R^{21}$ is preferably H or Cl and $R_{22}$ is preferably an alkyl or amido group. $R_{23}$ is preferably an amido group and $R_{24}$ is preferably hydrogen. Q" is hydrogen or a leaving group which is split off during the reaction with the oxidized developer. A detailed list of cyan couplers is to be found in U.S. Pat. No. 4,456,681.

Examples of customary cyan couplers are the following:
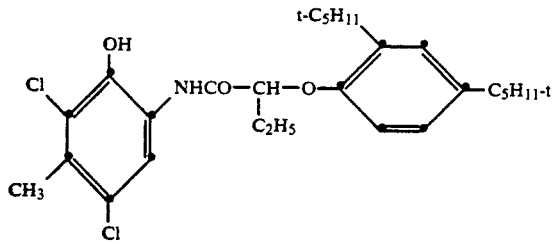
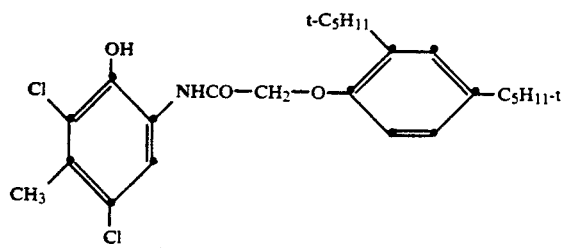
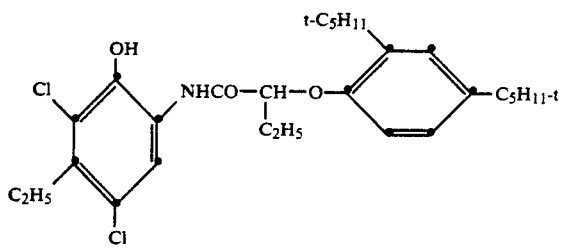
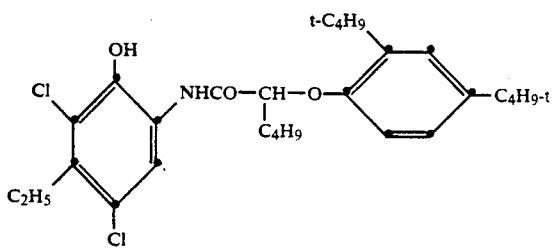
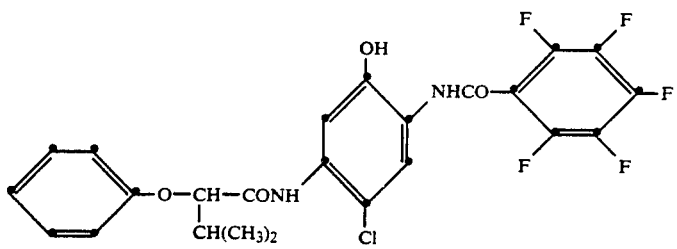
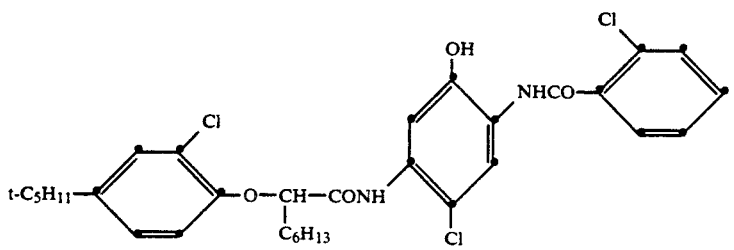
Further examples of cyan couplers are to be found in the following U.S. Pat. No.: 2,369,929, 2,423,730, 2,434,272, 2,474,293, 2,521,908, 2,698,794, 2,706,684, 2,772,162, 2,801,171, 2,895,826, 2,908,573, 3,034,892, 3,046,129, 3,227,550, 3,253,294, 3,311,476, 3,386,301, 3,419,390, 3,458,315, 3,476,560, 3,476,563, 3,516,831, 3,560,212, 3,582,322, 3,583,971, 3,591,383, 3,619,196, 3,632,347, 3,652,286, 3,737,326, 3,758,308, 3,839,044, 3,880,661, 4,004,929, 4,124,396, 4,333,999, 4,463,086 and 4,456,681.

The colour developers usually employed for colour photography materials are p-dialkylaminoanilines. Examples of these are 4-amino-N,N-diethylaniline, 3-methyl-4-amino-N,N-diethylaniline, 4-amino-N-ethyl-N-α-hydroxyethylaniline, 3-methyl-4-amino-N-ethyl-N-α-hydroxyethylaniline, 3-methyl-4-amino-N-ethyl-N-α-methanesulphonamidoethylaniline, 3-methyl-4-amino-N-ethyl-N-α-methoxyethyl-aniline, 3-α-methanesulphonamidoethyl-4-amino-N,N-diethylaniline, 3-methoxy-4-amino-N-ethyl-N-α-hydroxyethylaniline, 3-methoxy-4-amino-N-ethyl-N-α-methoxyethylaniline, 3-acetamido-4-amino-N,N-diethylaniline, 4-amino-N,N-dimethylaniline, N-ethyl-N-α-[α-(α-methoxyethoxy)ethoxy]ethyl-3-methyl-4-aminoaniline, N-ethyl-N-α-(α-methoxyethoxy)ethyl-3-methyl-4-aminoaniline and the salts of such compounds, for example sulfates, hydrochlorides or toluenesulfonates.

The stabilizers according to the invention can be incorporated into the colour photography material together with the colour coupler and if appropriate further additives by predissolving them in high-boiling organic solvents. Solvents which have a boiling point above 160° C. are preferably used. Typical examples of such solvents are the esters of phthalic acid, phosphoric acid, citric acid, benzoic acid or fatty acids, and alkylamides and phenols.

A low-boiling solvent is usually additionally also used in order to facilitate incorporation of the additives into the colour photography material. Examples of such solvents are esters, for example ethyl acetate, alcohols, for example butanol, ketones, for example methyl isobutyl ketone, chlorohydrocarbons, for example methylene chloride, or amides, for example dimethylforrnamide. If the additives themselves are liquid, they can also be incorporated into the photographic material without the aid of solvents.

Further details on high-boiling solvents which can be used are to be found in the following Patent Specifications:

Phosphates: GB-A-791,219, BE-A-755,248 and JP-A-76/76739, 78/27449, 78/218,252, 78/97573, 79/148,113, 82/216,177, 82/93323 and 83/ 216,177. Phthalates: GB-A-791,219 and JP-A-77/98050, 82/93322, 82/216,176, 82/218,251, 83/24321, 83/45699 and 84/79888. Amides: GB-A-791,219, JP-A-76/105,043, 77/13600, 77/61089 and 84/189,556 and U.S. Pat. No. 928,741. Phenols: GB-A-820,329, FR-A-1,200,657 and JP-A-69/69946, 70/3818, 75/123,026, 75/82078, 78/17914, 78/21166, 82/212,114 and 83/45699.

Other oxygen-containing compounds: U.S. Pat. No. 3,748,141 and 3,779,765, JP-A-73/75126, 74/101,114, 74/10115, 75/101,625, 76/76740 and 77/61089 and BE-A-826,039.

Other compounds: JP-A-72/115,369, 72/130,258, 73/127,521, 73/76592, 77/13193, 77/36294 and 79/95233 and Research Disclosure 82/21918.

The amount of high-boiling solvent is in the range from 0.1 to 300%, preferably 10 to 100%, based on the colour coupler.

The photographic layers can furthermore contain colour fog inhibitors. These prevent the formation of colour fogs, such as are formed, for example, by reaction of the coupler with unintentionally oxidized developer or with by-products of the colour formation process. Such colour fog inhibitors are usually hydroquinone derivatives, but they can also be derivatives of aminophenols, of gallic acid or of ascorbic acid. Typical examples of these are to be found in the following Patent Specifications: U.S. Pat. Nos. 2,360,290, 2,336,327, 2,403,721, 2,418,613, 2,675,314, 2,701,197, 2,704,713, 2,728,659, 2,732,300 and 2,735,365; EP-A-124,877; and JP-A-75/92988, 75/92989, 75/93928, 75/110,337 and 77/146,235.

The photographic layers can also contain so-called DIR couplers which give colourless compounds with the oxidized developer. They are added to improve the sharpness and grain structure of the colour pictures.

The photographic layers can also contain UV absorbers. These filter out the UV light and thus protect the dyes, the couplers or other components from photodegradation. Examples of such UV absorbers are 2-(2-hydroxyphenyl)-benzotriazoles, 2-hydroxybenzophenones, salicylic acid esters, acrylonitrile derivatives or thiazolines. Such UV absorbers are described in more detail, for example, in the following Patent Specifications: U.S. Pat. Nos. 3,314,794, 3,352,681, 3,705,805, 3,707,375, 4,045,229, 3,700,455, 3,533,794, 3,698,907, 3,705,805 and 3,738,837 and JP-A-71/2784. Preferred UV absorbers are the 2-(2-hydroxyphenyl)-benzotriazoles.

The photographic layers can also contain phenolic compounds which act as light stabilizers for the colour picture and as agents against colour fog. They can be contained in a photosensitive layer (colour layer) or in an intermediate layer, by themselves or together with other additives. Such compounds are described in more detail in the following Patent Specifications: U.S. Pat. Nos. 3,700,455, 3,591,381, 3,573,052, 4,030,931, 4,174,220, 4,178,184, 4,228,235, 4,279,990, 4,346,165, 4,366,226, 4,447,523, 4,528,264, 4,581,326, 4,562,146 and 4,559,297; GB-A-1,309,277, 1,547,302, 2,023,862, 2,135,788, 2,139,370 and 2,156,091; DE-A-2,301,060, 2,347,708, 2,526,468, 2,621,203 and 3,323,448; DD-A-200,691 and 214,468; EP-A-106,799, 113,124, 125,522, 159,912, 161,577, 164,030, 167,762 and 176,845; JP-A-74/134,326, 76/ 127,730, 76/30462, 77/3822, 77/154,632, 78/10842, 79/48535, 79/70830, 79/73032, 79/147,038, 79/154,325, 79/155,836, 82/142,638, 83/224,353, 84/5246, 84/72443, 84/87456, 84/192,246, 84/192,247, 84/204,039, 84/204,040, 84/212,837, 84/220,733, 84/222,836, 84/228,249, 86/2540, 86/ 8843, 86/18835, 86/18836, 87/11456, 87/42245, 87/62157 and 86/6652 and in Research Disclosure 79/17804.

The photographic layers can also contain certain phosphorus-III compounds, in particular phosphites and phosphonites. These function as light stabilizers for the colour pictures and as a dark storage stabilizer for magenta couplers. They are preferably added to the high-boiling solvents, together with the coupler. Such phosphorus-III compounds are described in more detail in the following Patent Specifications: U.S. Pat. No. 4,407,935, U.S. Pat. No. 4,436,811, EP-A-181,289, JP-A-73/32728, JP-A-76/1420 and JP-A-55/67741.

The photographic layers can also contain organometallic complexes which are light stabilizers for the colour pictures, in particular for the magenta dyes. Such compounds and combination thereof with other additives are described in more detail in the following Patent Specifications: U.S. Pat. Nos. 40,050,938, 4,239,843, 4,241,154, 4,242,429, 4,241,155, 4,242,430, 4,273,854, 4,246,329, 4,271,253, 4,242,431, 4,248,949, 4,245,194, 4,268,605, 4,246,330, 4,269,926, 4,245,018, 4,301,223, 4,343,886, 4,346,165 and 4,590,153; JP-A-81/167,138, 81/168,652, 82/30834 and 82/161,744; EP-A-137,271, 161,577 and 185,506; and DE-A-2,853,865.

The photographic layers can also contain hydroquinone compounds. These act as light stabilizers for the colour couplers and for the colour pictures and as trapping agents for oxidized developer in intermediate layers. They are used in particular in the magenta layer. Such hydroquinone compounds and combinations thereof with other additives are described in more detail in the following Patent Specifications: U.S. Pat. Nos. 2,360,290, 2,336,327, 2,403,721, 2,418,613, 2,675,314, 2,701,197, 2,710,801, 2,732,300, 2,728,659, 2,735,765, 2,704,713, 2,937,086, 2,816,028, 3,582,333, 3,637,393, 3,700,453, 3,960,570, 3,935,016, 3,930,866, 4,065,435, 3,982,944, 4,232,114, 4,121,939, 4,175,968, 4,179,293, 3,591,381, 3,573,052, 4,279,990, 4,429,031, 4,346,165, 4,360,589, 4,356,167, 4,385,111, 4,416,978, 4,430,425, 4,277,558, 4,489,155, 4,504,572 and 4,559,297; FR-A-885,982; GB-A-891,158, 1,156,167, 1,363,921, 2,022,274, 2,066,975, 2,071,348, 2,081,463, 2,117,526 and 2,156,091; GB-A-2,408,168, 2,726,283, 2,639,930, 2,901,520, 3,308,766, 3,320,483 and 3,323,699; DE-A-216,476, 214,468 and 214,469, EP-A-84290, 110,214, 115,305, 124,915, 124,877, 144,288, 147,747, 178,165 and 161,577; and JP-A-75/33733, 75/21249, 77/128,130, 77/146,234, 79/70036, 79/133,131, 81/83742, 81/87040, 81/109,343, 83/134,628, 82/22237, 82/112,749, 83/17431, 83/21249, 84/75249, 84/149,348, 84/182,785, 84/180,557, 84/189,342, 84/228,249, 84/101,650, 79/24019, 79/2582, 86/48856, 86/48857, 86/27539, 86/6652, 86/72040, 87/11455 and 87/62157 and in Research Disclosure 79/17901, 79/17905, 79/18813, 83/22827 and 84/24014.

The photographic layers can also contain derivatives of hydroquinone ethers. These compounds act as light stabilizers and are particularly suitable for stabilizing magenta dyes. Such compounds and combination thereof with other additives are described in more detail in the following patent specifications: U.S. Pat. Nos. 3,285,937, 3,432,300, 3,519,429, 3,476,772, 3,591,381, 3,573,052, 3,574,627, 3,573,050, 3,698,909, 3,764,337, 3,930,866, 4,113,488, 4,015,990, 4,113,495, 4,120,723, 4,155,765, 4,159,910, 4,178,184, 4,138,259, 4,174,220, 4,148,656, 4,207,111, 4,254,216, 4,314,011, 4,273,864, 4,264,720, 4,279,990, 4,332,886, 4,436,165, 4,360,589, 4,416,978, 4,385,111, 4,459,015 and 4,559,297; GB-A-1,347,556, 1,366,441, 1,547,392, 1,557,237 and 2,135,788; DE-A-3,214,567; DD-214,469; EP-A-161,577, 167,762, 164,130 and 176,845; and JP-A-76/123,642, 77/35633, 77/147,433, 78/126, 78/10430, 78/53321, 79/24019, 79/25823, 79/48537, 79/44521, 79/56833, 79/70036, 79/70830, 79/73032, 79/95233, 79/145,530, 80/21004, 80/50244, 80/52057, 80/70840, 80/139,383, 81/30125, 81/151,936, 82/34552, 82/68833, 82/204,036, 82/204,037, 83/134,634, 83/207,039, 84/60434, 84/101,650, 84/87450, 84/149,348, 84/182,785, 86/72040, 87/11455, 87/62157, 87/63149, 86/2151, 86/6652 and 86/48855 and in Research Disclosure 78/17051.

The efforts to develop colour photography materials in an even shorter time and at the same time to use chemicals which are easier to handle and pollute the environment less has led to considerable restrictions in the choice of the components of the system. Thus, silver halide emulsions used are those which are based largely or entirely on silver chloride, which means that the development time is shortened. It has furthermore been found that developer systems can be used largely or entirely without benzyl alcohol, without the colour density being reduced. This renders possible developer concentrates of few constituents, with shorter mixing times and with a lower toxicity of the spent developer. In order to achieve this aim of shortening the development time and reducing the benzyl alcohol, the following additives can be used:

a) N-substituted hydroxylamines as antioxidants instead of the customary hydroxylamines, b) development accelerators, for example 1-aryl-3-pyrazolones, hydrazine derivatives, quaternary ammonium and phosphonium compounds or polyoxyalkylene compounds, c) triethanolamine as tar-combating agents, d) lithium salts, for example those of polystyrenesulfonates, and e) aromatic polyhydroxy compounds, for example sodium 5,6-dihydroxy-1,2,4-benzenetrisulfonate.

The compounds of the formula I and II can also be used in such rapidly-developing systems, such as in photographic layers based on silver chloride emulsions, and in systems which are developed entirely or largely without benzyl alcohol.

The following examples illustrate the preparation and use of the novel compounds in detail. In these, parts and percentages are parts by weight and percentages by weight. The temperatures are stated in °C.

EXAMPLE 1:

27.0 g of cis-2,6-diphenylthian-4-ol (melting point 155°–156°, prepared in accordance with the method of C.A.R. Baxter, D.A. Whiting/J. Chem. Soc. 1968, 1176) and 27.8 g of 3-(3,5-di-tert-butyl-4-hydroxyphenyl)-propionic acid are introduced into 350 ml of toluene, with stirring. After addition of 1.5 g of p-toluenesulfonic acid, the reaction mixture is heated to reflux for 12 hours, using a water separator. After cooling, the reaction solution is washed three times with 100 ml of water each time, dried over $Na_2SO_4$ and evaporated in vacuo. The residue is recrystallized from ethanol. 4-[3-(3,5-Di-tert-butyl-4-hydroxyphenyl)-propionyloxy]-cis-2,6-diphenylthiane, which melts at 110° (compound No. 10), is obtained.

The esters listed in Table 1 are prepared in an analogous manner from the respective thiane-alcohols and phenolic carboxylic acids.

TABLE 1

In this table: Ph = phenyl
+ = tert-butyl

| Structural formula | Compound No. | Melting point |
|---|---|---|
| S⟨ring⟩–OOC–⟨ring⟩(X)(X)–OH | 1 | 114° |

TABLE 1-continued

In this table: Ph = phenyl
+ = tert-butyl

| Structural formula | Compound No. | Melting point |
|---|---|---|
| [thiane-OOC-CH₂CH₂-phenyl(di-t-Bu)-OH] | 2 | 76° |
| [2,6-di-Me thiane-OOC-phenyl(di-t-Bu)-OH] | 3 | 149° |
| [2,6-di-Me thiane-OOC-CH₂CH₂-phenyl(di-t-Bu)-OH] | 4 | 82° |
| [2,6-di-Me sulfoxide thiane-OOC-CH₂CH₂-phenyl(di-t-Bu)-OH] | 5 | 114° |
| [2,6-di-Me sulfone thiane-OOC-CH₂CH₂-phenyl(di-t-Bu)-OH] | 6 | 158° |
| [2,6-di-Me thiane-OOC-(CH₂)₃-C(CH₃)₂-phenyl(OH)(OCH₃)] | 7 | oil |
| [2,6-di-Ph thiane-OOC-phenyl(di-t-Bu)-OH] cis/trans | 9a<br>9b | 102°<br>184° |
| [2,6-di-Ph thiane-OOC-CH₂CH₂-phenyl(di-t-Bu)-OH] | 10 | 110° |

TABLE 1-continued

In this table: Ph = phenyl
+ = tert-butyl

| Structural formula | Compound No. | Melting point |
|---|---|---|
| [structure with SO₂, two Ph substituents, -OOC-CH₂CH₂-phenyl with two tert-butyl groups and OH] | 12 | 188–190° |
| [structure with SO₂, two Ph substituents, -OOC-CH₂CH₂-phenyl with CH₃, tert-butyl and OH] | 13 | 116–118° |
| [structure with thiopyran S, two 4-Cl-phenyl groups, O-C(=O)-phenyl with two tert-butyl and OH] | 34 | resin |
| [structure with thiopyran S, two 4-Cl-phenyl groups, O-C(=O)-CH₂CH₂-phenyl with two tert-butyl and OH] | 35 | 157° |
| [structure with thiopyran S, two 4-Cl-phenyl groups, O-C(=O)-CH₂CH₂-phenyl with CH₃, tert-butyl and OH] | 36 | resin |
| [structure with thiopyran S, two 4-CH₃O-phenyl groups, O-C(=O)-CH₂CH₂-phenyl with two tert-butyl and OH] | 37 | resin |

TABLE 1-continued

In this table: Ph = phenyl
+ = tert-butyl

| Structural formula | Compound No. | Melting point |
|---|---|---|
| (structure) | 42 | 144–146° |
| (structure) | 43 | 97–99° |

EXAMPLE 2

Transesterification 115.4 g of 3-ethyl-3-hydroxymethyl-8,10-diphenyl-1,5-dioxa-9-thiaspiro[5.5]undecane and 88.6 g of methyl 3-(3,5-di-tert-butyl-4-hydroxyphenyl)propionate are introduced into 800 ml of benzine (boiling range 110°–140°). About 50 ml of benzine are distilled off and the solution is allowed to cool to about 80°. After addition of 0.3 g of lithium amide, the reaction mixture is heated under a gentle stream of nitrogen until the methanol formed-together with a little benzine-distils over. After about 4 hours, the mixture is allowed to cool somewhat and 0.8 g of glacial acetic acid is added. After 10 minutes, 10 g of Tonsil are added and the mixture is stirred for a further 5 minutes and filtered. 3-[3-(3,5-Di-tert-butyl-4-hydroxyphenyl)-propionyloxymethyl]-3-ethyl-8,10-diphenyl-1,5-dioxa-9-thiaspiro[5.5]undecane crystallizes out of the filtrate on cooling and melts at 122° after drying (compound No. 19).

The esters listed in Table 2 are prepared in an analogous manner from the respective thiane-alcohols and methyl phenolcarboxylates.

TABLE 2

| Structural formula | Compound No. | Melting point |
|---|---|---|
| (structure) | 15 | resin |
| (structure) | 16 | resin |

TABLE 2-continued

| Structural formula | Compound No. | Melting point |
|---|---|---|
| (structure with dioxane ring bearing two Ph groups and S, linked via O-CH₂OOC-CH₂CH₂- to 2-methyl-4-hydroxyphenyl with two X substituents) | 17 | resin |
| (dioxane ring with S, 2,6-diphenyl, linked via O-C(C₂H₅)(CH₂OOC-)-O to 4-hydroxyphenyl with two X substituents) | 18 | 142–144° |
| (dioxane ring with S, 2,6-diphenyl, linked via O-C(C₂H₅)(CH₂OOC-CH₂CH₂-)-O to 2-methyl-4-hydroxyphenyl with two X) | 20 | 123° |
| (dioxane ring with SO₂, 2,6-diphenyl, linked via O-C(C₂H₅)(CH₂OOC-CH₂CH₂-)-O to 4-hydroxyphenyl with two X) | 21 | resin |
| (dioxane ring with SO₂, 2,6-diphenyl, linked via O-C(C₂H₅)(CH₂OOC-CH₂CH₂-)-O to 2-methyl-4-hydroxyphenyl with two X) | 22 | resin |
| (dioxane ring with S, 2,6-diphenyl, linked via O-C(C₂H₅)(CH₂OOC-CH₂-O-)-O to 4-hydroxyphenyl with two X) | 23 | oil |
| (dioxane ring with S, 2,6-diphenyl, linked via O-C(C₂H₅)(CH₂OOC-(CH₂)₃-C(CH₃)₂-)-O to 2-hydroxy-5-methylphenyl) | 26 | oil |

TABLE 2-continued

| Structural formula | Compound No. | Melting point |
|---|---|---|
| (structure) | 27 | oil |
| (structure) | 28 | oil |
| (structure) | 29 | oil |
| (structure) | 30 | oil |
| (structure) | 31 | oil |
| (structure) | 34 | 191–193° |

TABLE 2-continued
| Structural formula | Compound No. | Melting point |
|---|---|---|
| 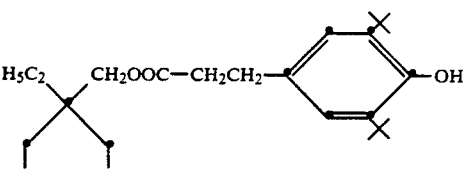 | 38 | resin |
| 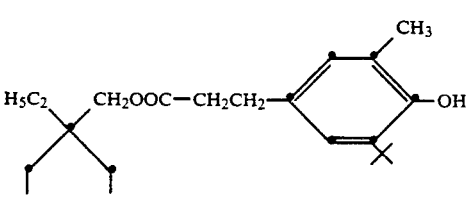 | 40 | resin |
| 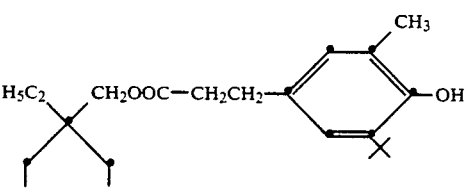 | 41 | resin (85–95°) |
| 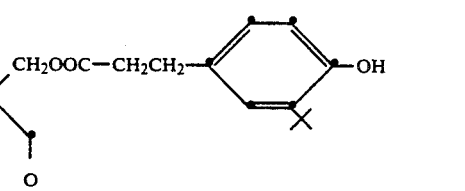 | 45 | resin |

TABLE 2-continued
| Structural formula | Compound No. | Melting point |
|---|---|---|
| 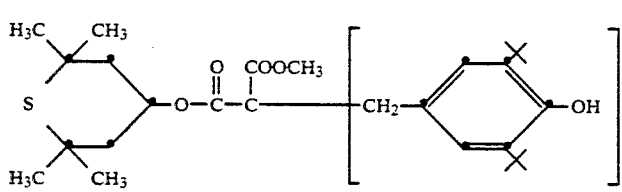 | 50 | 163° |
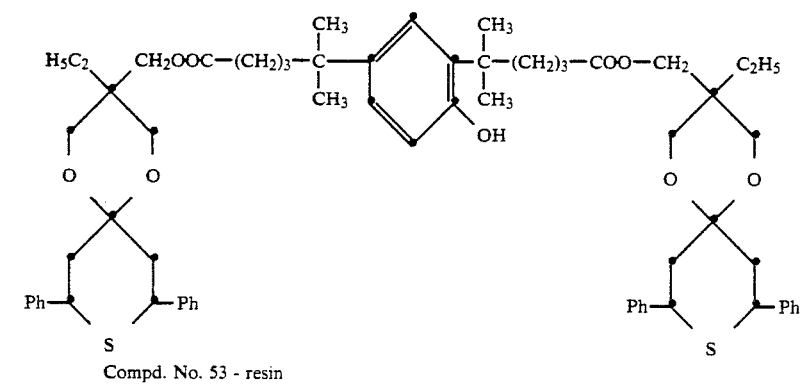
Compd. No. 53 - resin
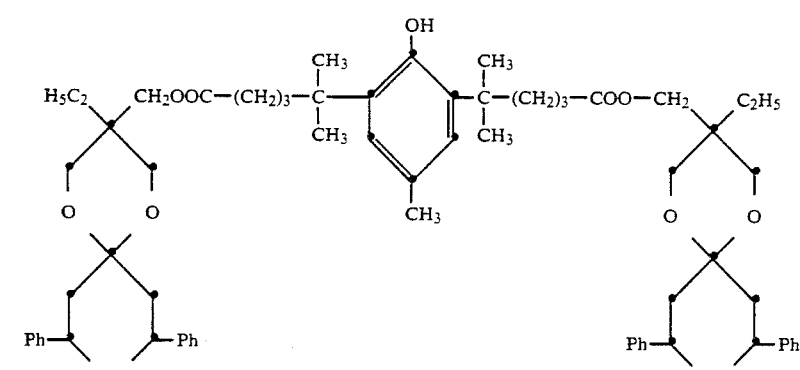
Compd. No. 54 - resin
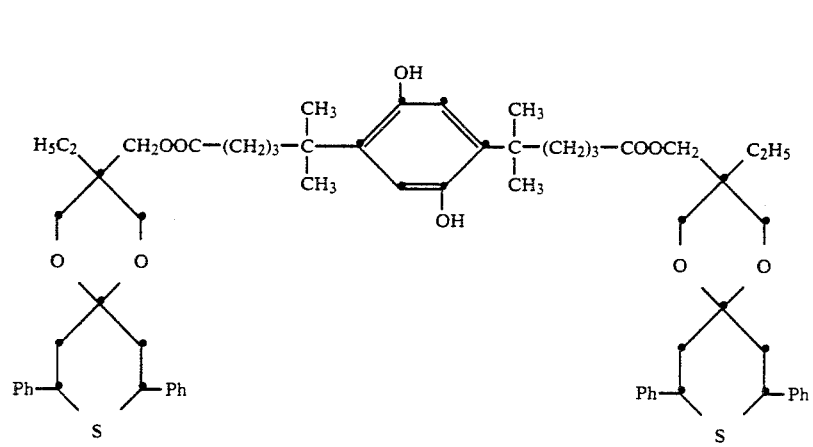
Compd. No. 55 - resin

TABLE 2-continued

| Structural formula | Compound No. Melting point |
|---|---|
| Compd. No. 56 - m.p. 69° | |
| Compd. No. 57 - viscous oil | |
| Comd. No. 59 - m.p. 168° | |

In this table: Ph = phenyl + = tert-butyl

EXAMPLE 3

Acylhydrazones 12.5 g of 3-(3-methyl-4-tert-butyl-4-hydroxyphenyl)-propionic acid hydrazide and 13.6 g of 2,6-diphenyl-4-oxothiane are warmed to reflux in 300 ml of ethanol for 3 hours. The crude product which crystallizes out on cooling is filtered off and recrystallized from 500 ml of xylene. The resulting N-[-(3-methyl-5-tert-butyl-4-hydroxyphenyl)-propionylamido]-2,6-diphenyl-4-iminothiane of the formula

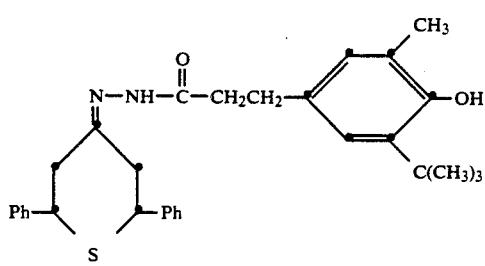

melts at 211°-212° after drying in vacuo (compound No. 48).

N-[-(3,5-Di-tert-butyl-4-hydroxyphenyl)-propionylamido]-2,6-diphenyl-4-iminothiane, which melts at 266°, is prepared analogously from 14.6 g of 3-(3,5-di-tert-butyl-4-hydroxyphenyl)-propionic acid hydrazide and 13.4 g of 2,6-diphenyl-4-oxothiane (compound No. 49).

EXAMPLE 4

Hydroxybenzylation of malonates 19 g of di-(2,2,6,6-tetramethylthian-4-yl)-malonate and 33.5 g of N,N-diethyl S-(3,5-di-tert-butyl-4-hydroxybenzyl) -dithiocarbamate are warmed to 50° in 150 ml of isopropanol. A solution of 3.6 g of NaOH in 20 ml of water is added dropwise at this temperature in the course of 30 minutes. The product starts to crystallize during the course of this. The mixture is heated at 50° for 1 hour and to reflux for 3 hours and then cooled to room temperature. The product which has precipitated is filtered off and recrystallized from acetone/acetonitrile. The resulting di(2,2,6,6-tetramethylthian-4-yl) bis-(3,5-di-tert-butyl-4-hydroxybenzyl)-malonate of the formula

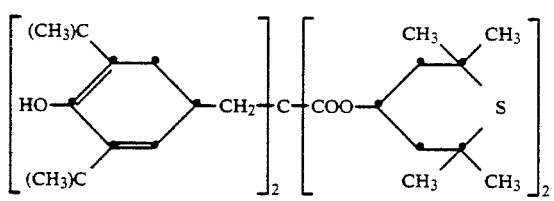

has a melting point of 220° (compound No. 51).

EXAMPLE 5

Acylation of the phenol group 1.5 g of -3-[3-(3-tert-butyl-5-methyl-4-hydroxyphenyl)-propionyloxymethyl]-3-methyl-8,10-diphenyl-1,5-dioxa-9thiaspiro[5.5]undecane are dissolved in 20 ml of toluene. 2 ml of dimethylformamide and 0.63 g of trimethylamine are added. 0.6 g of methyl oxalyl chloride in 10 ml of toluene are added dropwise, while cooling to 0°. The mixture is stirred at room temperature for 6 hours. 20 ml of water are then added and the organic phase is separated off, dried and evaporated. The crude product of the formula

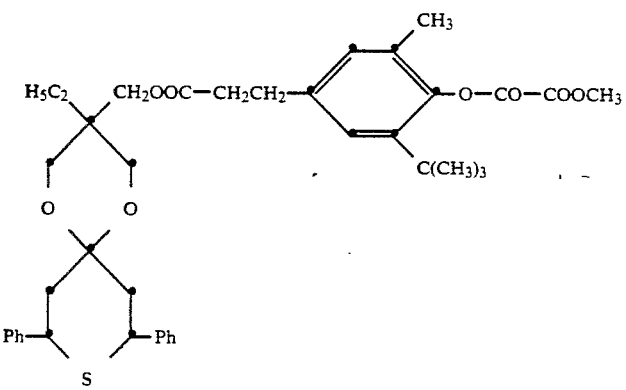

remains as a residue in the form of a colourless oil (compound No. 46). The compound of the formula

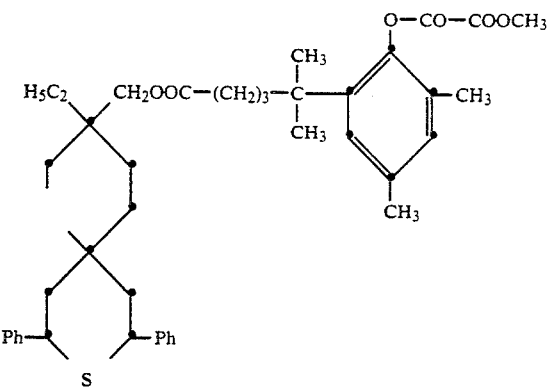

is obtained as a yellowish oil (compound No. 52) in an analogous manner by reaction of 1.43 g of 3-[5-(3,5-dimethyl-2-hydroxyphenyl)-5-methylhexanoyloxymethyl]-3-ethyl-8,10-diphenyl-1,5-dioxa-9-thiaspiro[5.5]undecane.

EXAMPLE 6

Silylation of the phenol group 1.5 g of 3-[3-(3-tert-butyl-5-methyl-4-hydroxyphenyl)-propionyloxymethyl]-8,10-diphenyl-1,5-dioxa-9-thiaspiro[5.5]undecane and 0.94 g of 1,8-diazabicyclo[5.4.0]undec-7-ene are dissolved in 20 ml of toluene. 0.54 g of trimethylchlorosilane in 10 ml of toluene is added dropwise, while cooling to 0°. The mixture is stirred at room temperature for 6 hours, 20 ml of water are then added and the organic phase is separated off, dried and evaporated. The oily residue is purified by chromatography on an $Al_2O_3$ column. Hexane/ethyl acetate 9:1 is used as the eluting agent. The compound of the formula

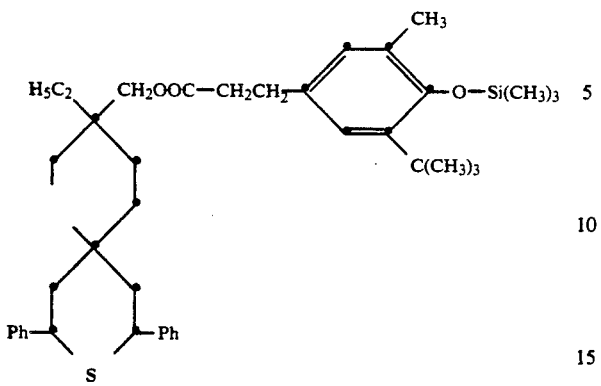

is obtained as a colourless oil (compound No. 47).

EXAMPLE 7

Stabilization of a yellow layer 0.087 g of the yellow coupler of the formula

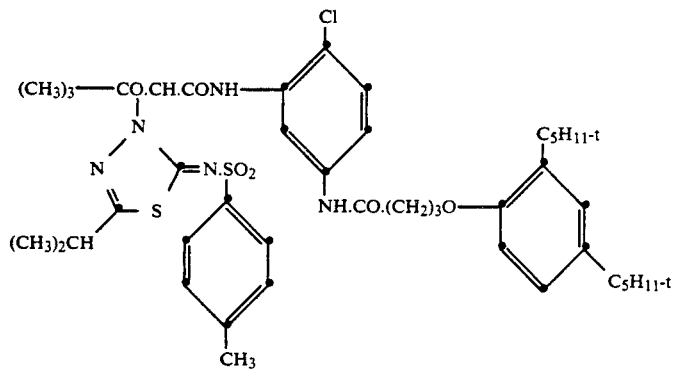

and 0.029 g of one of the light stabilizers shown in the following tables are dissolved in 2 ml of a mixture of dibutyl phthalate/ethyl acetate (1.5 g/100 ml). 9 ml of a 2.3% aqueous gelatin solution which has been brought to a pH of 6.5 and contains 1.744 g/l of the wetting agent Nekal ®BX (Na diisobutylnaphthalene-sulfonate) are added to 1 ml of this solution. The mixture is then emulsified by means of ultra-sound for 3 minutes.

2 ml of a silver bromide emulsion with a silver content of 6 g per litre and 1 ml of a 0.7% aqueous solution of cyanuric acid dichloride as a gelatin hardener are added to 5 ml of the coupler emulsion thus obtained and the mixture is poured onto a plastic-coated paper of 13×18 cm. After a hardening time of 7 days, the samples are exposed with 125 lux.s through a silver step wedge and then processed in the Ektaprint process from Kodak.

The colour step wedges thus obtained are irradiated in an Atlas Weather-Ometer behind a UV filter (Kodak 2C) with a 2500 W xenon lamp with a total of 60 kilojoules per $cm^2$.

The percentage decreases in colour density for an original colour density of 1.0 are shown in the following Tables 3 and 4.

TABLE 3

| Stabilizer Compound No. | Loss in density in % (behind UV filter) |
|---|---|
| none | 23 |
| 18 | 11 |
| 42 | 12 |
| 43 | 11 |
| 44 | 12 |

TABLE 4

| Stabilizer Compound No. | Loss in density in % (behind UV filter) |
|---|---|
| none | 27 |
| 9a | 10 |
| 10 | 9 |
| 12 | 15 |
| 13 | 11 |
| 15 | 8 |
| 16 | 11 |
| 17 | 8 |
| 19 | 9 |
| 20 | 8 |
| 21 | 15 |
| 22 | 12 |
| 26 | 12 |
| 28 | 7 |
| 29 | 13 |
| 30 | 12 |
| 31 | 12 |
| 34 | 12 |
| 35 | 9 |
| 36 | 10 |
| 37 | 14 |
| 38 | 8 |
| 40 | 8 |
| 41 | 8 |
| 46 | 11 |
| 47 | 13 |
| 48 | 14 |
| 53 | 12 |
| 54 | 14 |
| 55 | 13 |
| 56 | 10 |
| 57 | 14 |
| 58 | 11 |
| 59 | 9 |

EXAMPLE 8

0.091 g of the yellow coupler of the formula

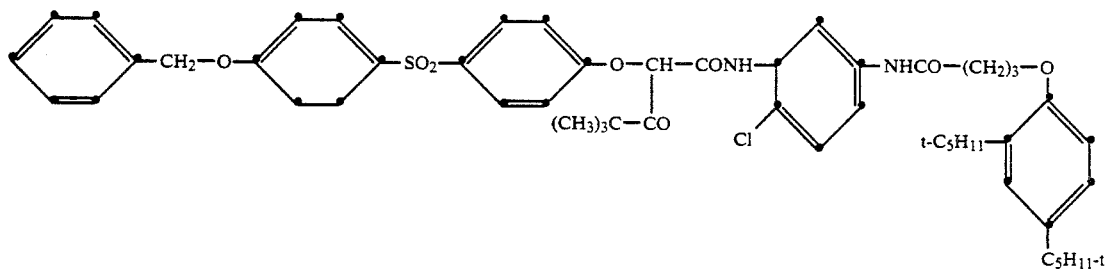

and 0.027 g of one of the light stabilizers shown in the following table are dissolved in 2 ml of a mixture of dibutyl phthalate/ethyl acetate (1.5 g/100 ml). 9 ml of a 2.3% aqueous gelatin solution which has been brought to a pH of 6.5 and contains 1.744 g/l of the wetting agent Nekal ®BX are added to 1 ml of this solution. The mixture is then emulsified by means of ultra-sound for 3 minutes.

2 ml of a silver bromide emulsion with a silver content of 6 g per litre and 1 ml of a 0.7% aqueous solution of cyanuric acid dichloride as a gelatin hardener are added to 5 ml of the coupler emulsion thus obtained and the mixture is poured onto plastic-coated paper of 13×18 cm. After a hardening time of 7 days, the samples are exposed with 125 lux.s through a silver step wedge and then processed in the Ektaprint 2 process from Kodak.

The colour step wedges thus obtained are irradiated in an Atlas Weather-Ometer behind a UV filter (Kodak 2C) with a 2500 W xenon lamp with a total of 60 kilojoules per cm².

The percentage decreases in colour density for an original colour density of 1.0 are shown in Table 5.

TABLE 5

| Stabilizer Compound No. | Loss in density in % (behind UV filter) |
|---|---|
| none | 18 |
| 9a | 10 |
| 10 | 10 |
| 19 | 8 |
| 22 | 10 |
| 34 | 9 |
| 35 | 9 |
| 38 | 11 |
| 40 | 8 |

EXAMPLE 9

0.076 g of the yellow coupler of the formula

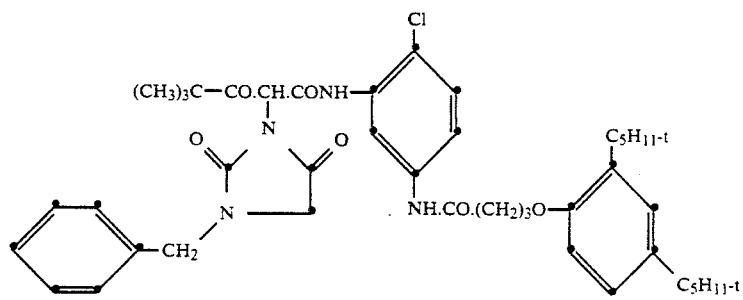

and 0.023 g of one of the light stabilizers shown in the following table are dissolved in 2 ml of a mixture of dibutyl phthalate/ethyl acetate (1.5 g/100 ml). 9 ml of a 2.3% aqueous gelatin solution which has been brought to a pH of 6.5 and contains 1.744 g/l of Nekal ®BX are added to 1 ml of this solution. The mixture is then emulsified by means of ultrasound for 3 minutes.

2 ml of a silver bromide emulsion with a silver content of 6 g per litre and 1 ml of a 0.7% aqueous solution of cyanuric acid dichloride as a gelatin hardener are added to 5 ml of the coupler emulsion thus obtained and the mixture is poured onto plastic-coated paper of 13×18 cm. After a hardening time of 7 days, the samples are exposed with 125 lux.s through a silver step wedge and then processed in the Ektaprint 2 process from Kodak.

The colour step wedges thus obtained are irradiated in an Atlas Weather-Ometer behind a UV filter (Kodak 2C) with a 2500 W xenon lamp with a total of 60 kilojoules per cm².

The percentage decreases in colour density for an original colour density of 1.0 are shown in the following Table 6.

TABLE 6

| Stabilizer Compound No. | Loss in density in % (behind UV filter) |
|---|---|
| none | 21 |
| 19 | 8 |
| 34 | 10 |
| 36 | 10 |
| 38 | 9 |
| 40 | 7 |

EXAMPLE 10

0.038 g of the magenta coupler of the formula

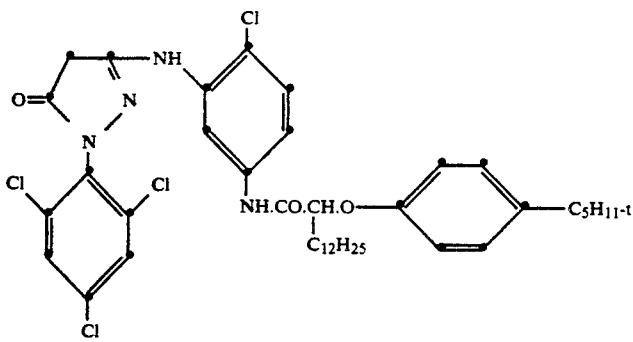

and 0.013 g of a light stabilizer shown in Table 7 are dissolved in 2 ml of a mixture of tricresyl phosphate/ethyl acetate (1 g/100 ml). 9 ml of a 2.3% aqueous gelatin solution which has been brought to a pH of 6.5 and contains 0.436 g/l of Nekal ®BX are added to 1 ml of this solution. The mixture is then emulsified by means of ultra-sound for 3 minutes.

2 ml of a silver bromide emulsion with a silver content of 6 g per litre and 1 ml of a 0.7% aqueous solution of cyanuric acid dichloride as a gelatin hardener are added to 5 ml of the coupler emulsion thus obtained and the mixture is poured onto a plastic-coated paper of 13×18 cm. After a hardening time of 7 days, the samples are exposed with 125 lux.s through a silver step wedge and then processed in the Ektaprint 2 process from Kodak.

The colour step wedges thus obtained are stored in a climate cabinet for 28 days at 75° C. and 60% relative atmospheric humidity. The following Table 7 shows the percentage increase in colour density for an original colour density of 1.0.

TABLE 7

| Stabilizer Compound No. | Increase in density in % (behind UV filter) |
| --- | --- |
| none | 41 |
| 9a | 28 |
| 18 | 28 |
| 42 | 31 |

EXAMPLE 11

0.025 g of the cyan coupler of the formula

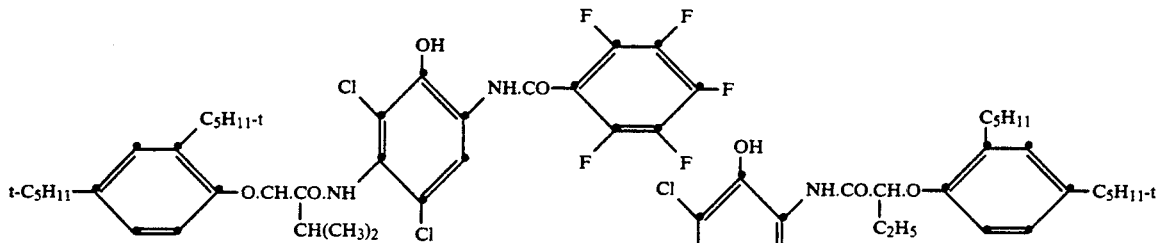

and 0.025 g of one of the light stabilizers shown in Table 8 are dissolved in 2 ml of a mixture of dibutyl phthalate/ethyl acetate (0.8 g/100 ml). 9 ml of a 2.3% aqueous gelatin solution which has been brought to a pH of 6.5 and contains 0.872 g/l of Nekal ®BX are added to 1 ml of this solution. The mixture is then emulsified by means of ultrasound for 3 minutes.

2 ml of a silver bromide emulsion with a silver content of 3 g per litre and 1 ml of a 0.7% aqueous solution of cyanuric acid dichloride as a gelatin hardener are added to 5 ml of the coupler emulsion thus obtained and the mixture is poured onto a plastic-coated paper of 13×18 cm. After a hardening time of 7 days, the samples are exposed with 125 lux.s through a silver step wedge and then processed in the Ektaprint 2 process from Kodak.

The colour step wedges thus obtained are irradiated in an Atlas Weather-Ometer behind a UV filter (Kodak 2C) with a 2500 W xenon lamp with a total of 60 kilojoules per cm$^2$.

The percentage decreases in colour density for an original colour density of 1.0 are shown in Table 8.

TABLE 8

| Stabilizer Compound No. | Loss in density in % (behind UV filter) |
| --- | --- |
| none | 29 |
| 18 | 19 |
| 20 | 17 |

EXAMPLE 12

0.025 g of the cyan coupler of the formula and 0.025 g of one of the light stabilizers shown in Table 9 are dissolved in 2 ml of a mixture of dibutyl phthalate/ethyl acetate (0.8 g/100 ml). 9 ml of a 2.3% aqueous gelatin solution which has been brought to a pH of 6.5 and contains 0.872 g/l of Nekal ®BX are added to 1 ml of this solution. The mixture is then emulsified by means of ultrasound for 3 minutes.

2 ml of a silver bromide emulsion with a silver content of 3 g per litre and 1 ml of a 0.7% aqueous solution of cyanuric acid dichloride as a gelatin hardener are added to 5 ml of the coupler emulsion thus obtained and the mixture is poured onto a plastic-coated paper of 13×18 cm. After a hardening time of 7 days, the samples are exposed with 125 lux.s through a silver step wedge and then processed in the Ektaprint 2 process from Kodak.

The colour step wedges thus obtained are stored in a climate cabinet for 28 days at 75° C. and 60% relative atmospheric humidity.

The percentage decreases in colour density for an original colour density of 1.0 are shown in Table 9.

TABLE 9

| Stabilizer Compound No. | Loss in density in % (behind the UV filter) |
|---|---|
| none | 50 |
| 18 | 30 |
| 9b | 31 |

EXAMPLE 13

0.031 g of the magenta coupler of the formula

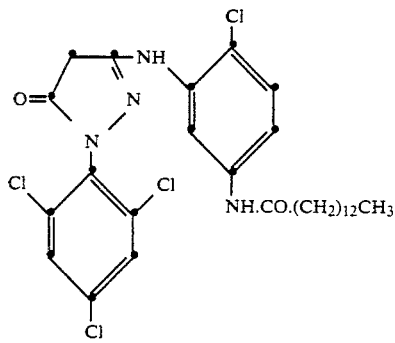

and the amount of one of the light stabilizers (or light stabilizer mixtures) shown in the following Table 10 are dissolved in 2 ml of a mixture of tricresyl phosphate/ethyl acetate (0.769 g/100 ml). 9.0 ml of a 2.3% aqueous gelatin solution which has been brought to a pH of 6.5 and contains 0.436 g/1 of the wetting agent Nekal ®BX (Na diisobutylnaphthalenesulfonate) are added to 1 ml of this solution. The mixture is then emulsified by means of ultra-sound for 3 minutes.

2 ml of a silver bromide emulsion with a silver content of 6 g per litre and 1.0 ml of a 0.7% aqueous solution of cyanuric acid dichloride as a gelatin hardener are added to 5.0 ml of the coupler emulsion thus obtained and the mixture is poured onto a plastic-coated paper of 13×18 cm. After a hardening time of 7 days, the samples are exposed with 125 lux.s through a silver step wedge and then processed in the Ektaprint 2 process from Kodak.

The colour step wedges thus obtained are irradiated in an Atlas Weather-Ometer behind a UV filter (Kodak 2C) with a 2500 W xenon lamp with a total of 60 kilojoules per cm².

The increase in the yellow colour density in the non-exposed portion of the step wedge is shown in the following Table 10 ($D_B$).

TABLE 10

| Stabilizer Compound No. | Amount (g) | $D_B$ |
|---|---|---|
| None | — | 16% |
| 10 | 0.011 | 7% |
| 19 | 0.011 | 8% |
| 10 + costabilizer A | 0.0055 0.0055 | 6% |
| 19 + costabilizer A | 0.0055 0.0055 | 5% | costabilizer A = phenolic compound of the formula

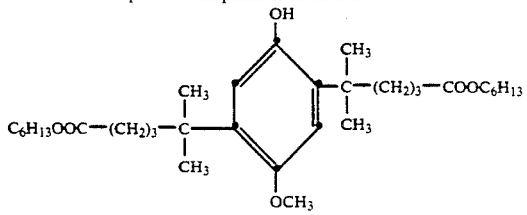

What is claimed is:

1. A method for the stabilization of colour photography recording materials containing at least one gelatin layer containing at least one silver halide and one dye coupler against light and thermal oxidation which comprises incorporating into at least one gelatin layer an effective stabilizing amount of at least one compound of the formula I or II

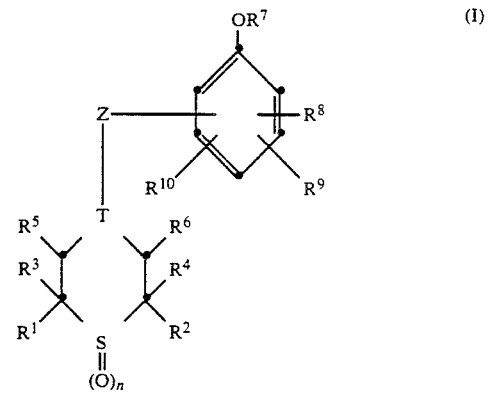

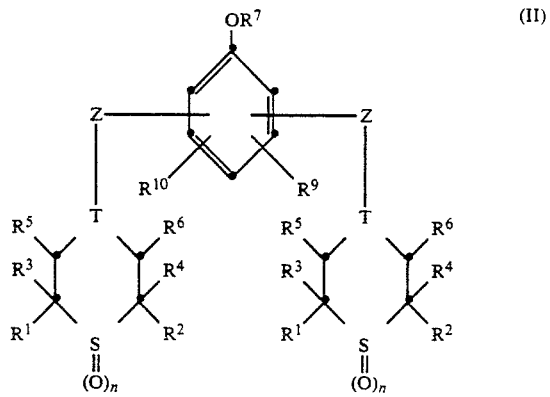

in which n is 0, 1 or 2, $R^1$ and $R^2$ independently of one another are hydrogen or methyl, $R^3$ and $R^4$ independently of one another are hydrogen, $C_1$–$C_4$alkyl, phenyl, thienyl or phenyl which is substituted by 1 or 2

$C_1$-$C_8$alkyl groups, cyclohexyl, phenyl, $C_7$-$C_9$phenylalkyl, hydroxyl, $C_1$-$C_{18}$alkoxy or halogen, $R^5$ and $R^6$ independently of one another are hydrogen, $C_1$-$C_4$alkyl, phenyl, —COO($C_1$-$C_{18}$alkyl), —CO—$CH_3$ or —CO—phenyl, $R^7$ is hydrogen, $C_1$-$C_8$alkyl or one of the groups —CO—$R^{11}$, —CO—COO($C_1$-$C_4$-alkyl), —$SO_2$—$R^{12}$, —CON($R^{13}$)($R^{14}$), —Si($R^{15}$)($R^{16}$)($R^{17}$) or

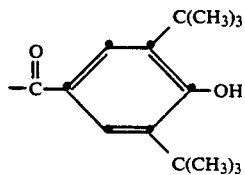

$R^8$ and $R^9$ independently of one another are hydrogen, $C_1$-$C_{12}$alkyl, $C_7$-$C_9$phenylalkyl, $C_5$-$C_8$cycloalkyl or phenyl, $R^{10}$ is hydrogen, —$OR^7$ or a group of the formula III

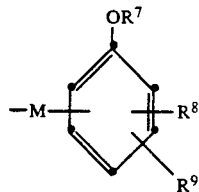

in which M is a direct bond, —O—, —S—, —S—S—, —$CH_2$—, —CH($C_1$-$C_8$alkyl)— or —C($CH_3$)$_2$—, $R^{11}$ is $C_1$-$C_{20}$alkyl, $C_3$-$C_{20}$alkenyl, $C_5$-$C_{12}$cycloalkyl, $C_7$-$C_{13}$phenylalkyl or $C_6$-$C_{10}$aryl, $R^{12}$ is $C_1$-$C_{12}$alkyl, $C_6$-$C_{10}$aryl or $C_7$-$C_{24}$alkylaryl, $R^{13}$ is hydrogen, $C_1$-$C_{12}$alkyl or cyclohexyl, $R^{14}$ is $C_1$-$C_{12}$alkyl, $C_6$-$C_{10}$aryl, $C_1$-$C_{12}$alkylsubstituted $C_6$-$C_{10}$aryl or cyclohexyl, or $R^{13}$ and $R^{14}$, together with the N atom, form a 5- or 6-membered saturated heterocyclic ring, $R^{15}$, $R^{16}$ and $R^{17}$ independently of one another are $C_1$-$C_{12}$alkyl, $C_3$-$C_{12}$alkenyl, phenyl, cyclohexyl or benzyl, T is a trivalent group which completes the ring to give a thiane ring and is one of the following groups:

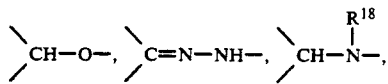

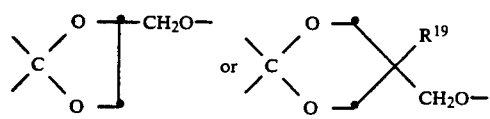

in which $R^{18}$ is hydrogen, $C_1$-$C_{12}$alkyl, benzyl, cyclohexyl or phenyl and $R^{19}$ is hydrogen or $C_1$-$C_4$alkyl, Z is a divalent bonding member between T and the phenol radical and is one of the following groups:

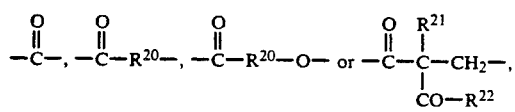

the carbonyl group of which is bonded to T and in which $R^{20}$ is $C_1$-$C_{14}$alkylene, $R^{21}$ is hydrogen, $C_1$-$C_1$-2alkyl, phenyl, $C_7$-$C_9$phenylalkyl or a group of the formula IV

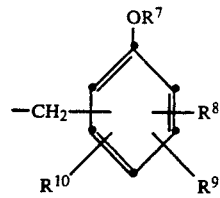

and $R^{22}$ is a group —O($C_1$-$C_4$alkyl) or a group of the formula V

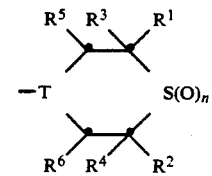

2. A method according to claim 1 wherein the said at least one compound is incorporated into at least the yellow layer of the colour photography material.

3. A colour photography recording material stabilized against light and thermal oxidation which comprises at least one gelatin layer containing at least one gelatin layer containing at least one silver halide and one dye coupler, at least one gelatin layer having incorporated therein an effective stabilizing amount of at least one compound of the formula I or II

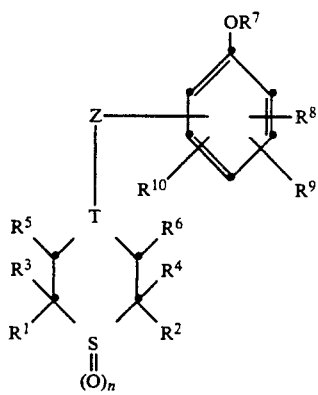

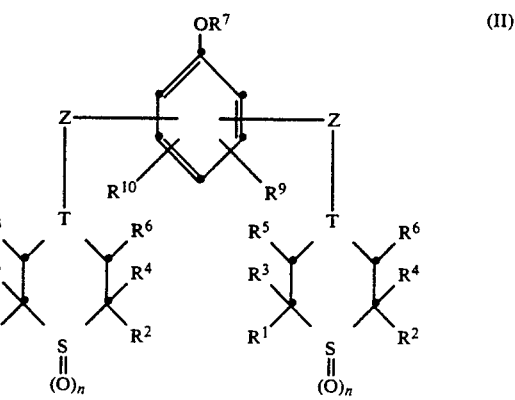

in which n is 0, 1 or 2, $R^1$ and $R^2$ independently of one another are hydrogen or methyl, $R^3$ and $R^4$ independently of one another are hydrogen, $C_1$-$C_4$alkyl, phenyl, thienyl or phenyl which is substituted by 1 or 2 $C_1$-$C_8$alkyl groups, cyclohexyl, phenyl, $C_7$-$C_9$phenylalkyl, hydroxyl, $C_1$-$C_{18}$alkoxy or halogen, $R^5$ and $R^6$ independently of one another are hydrogen, $C_1$-$C_4$alkyl, phenyl, —COO($C_1$-$C_{18}$alkyl), —CO—$CH_3$ or —CO—phenyl, $R^7$ is hydrogen, $C_1$-$C_8$alkyl or one of the groups —CO—$R^{11}$, —CO—COO($C_1$-$C_4$alkyl), —$SO_2$—$R^{12}$, —CON($R^{13}$)($R^{14}$), —Si($R^{15}$)($R^{16}$)($R^{17}$) or

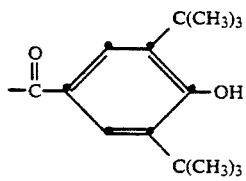

$R^8$ and $R^9$ independently of one another are hydrogen, $C_1$-$C_{12}$alkyl, $C_7$-$C_9$phenylalkyl, $C_5$-$C_8$cycloalkyl or phenyl, $R^{10}$ is hydrogen, —$OR^7$ or a group of the formula III

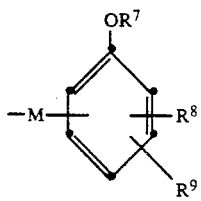

in which M is a direct bond, —O—, —S—, —S—S—, —$CH_2$—, —CH($C_1$-$C_8$alkyl)— or —C($CH_3$)$_2$—, $R^{11}$ is $C_1$-$C_{20}$alkyl, $C_3$-$C_{20}$alkenyl, $C_5$-$C_{12}$cycloalkyl, $C_7$-$C_{13}$phenylalkyl or $c_6$-$C_{10}$aryl, $R^{12}$ is $C_1$-$C_{12}$alkyl, $C_6$-$C_{10}$aryl or $C_7$-$C_{24}$alkylaryl, $R^{13}$ is hydrogen, $C_1$-$C_{12}$alkyl or cyclohexyl, $R^{14}$ is $C_1$-$C_{12}$alkyl, $C_6$-$C_{10}$aryl, $C_1$-$C_{12}$alkylsubstituted $C_6$-$C_{10}$aryl or cyclohexyl, or $R^{13}$ and $R^{14}$, together with the N atom, form a 5- or 6-membered saturated heterocyclic ring, $R^{15}$, $R^{16}$ and $R^{17}$ independently of one another are $C_1$-$C_{12}$alkyl, $C_3$-$C_{12}$alkenyl, phenyl, cyclohexyl or benzyl, T is a trivalent group which completes the ring to give a thiane ring and is one of the following groups:

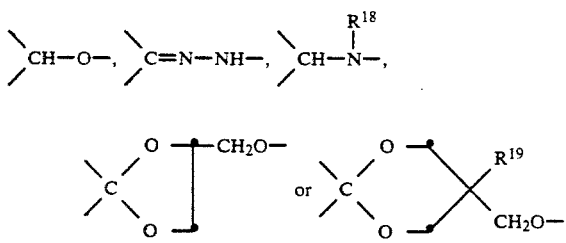

in which $R^{18}$ is hydrogen, $C_1$-$C_{12}$alkyl, benzyl, cyclohexyl or phenyl and $R^{19}$ is hydrogen or $C_1$-$C_4$alkyl, Z is a divalent bonding member between T and the phenol radical and is one of the following groups:

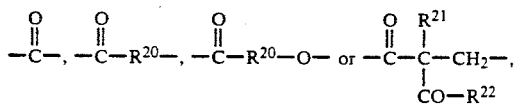

the carbonyl group of which bonded to T and in which $R^{20}$ is $C_1$-$C_{14}$alkylene, $R^{21}$ is hydrogen, $C_1$-$C_{12}$alkyl, phenyl, $C_7$-$C_9$phenylalkyl or a group of the formula IV

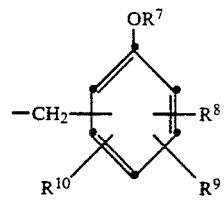

and $R^{22}$ is a group —O($C_1$-$C_4$alkyl) or a group of the formula V

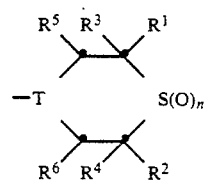

4. A colour photography recording material according to claim 3 wherein the said at least one compound is incorporated into at least the yellow layer of the material.

5. A colour photography recording material according to claim 3 in which n is 0 or 2, $R^1$ and $R^2$ are hydrogen or methyl, $R^3$ and $R^4$ independently of one another are methyl, phenyl, thienyl or phenyl which is substituted by one or two $C_1$-$C_4$alkyl groups, cyclohexyl, hydroxyl, $C_1$-$C_4$alkoxy or chlorine, $R^5$ and $R^6$ independently of one another are hydrogen, —COO($C_1$-$C_4$alkyl) or —$COCH_3$, $R^7$ is hydrogen or a group —CO—$R^{11}$, —CO—COO($C_1$-$C_4$alkyl), —Si($CH_3$)$_3$ or

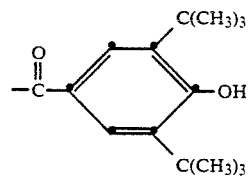

$R^8$ and $R^9$ independently of one another are $C_1$-$C_8$alkyl, $C_7$-$C_9$phenylalkyl, cyclohexyl or phenyl, $R^{10}$ is hydrogen, —$OR^7$ or a group of the formula III, in which M is —S—, —$CH_2$—, —CH($C_1$-$C_4$alkyl) or —C($CH_3$)$_2$—, $R^{11}$ is $C_1$-$C_{12}$alkyl or phenyl, T is one of the following trivalent groups:

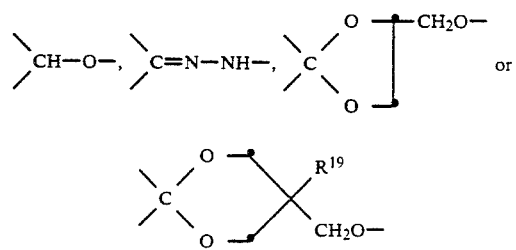

in which $R^{19}$ is $C_1$-$C_4$alkyl, and Z is one of the following divalent groups:

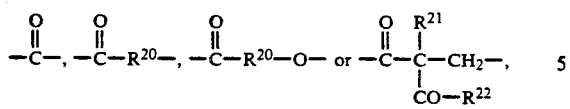

the carbonyl group of which is bonded to T and in which $R^{20}$ is $C_1$-$C_{14}$alkylene, $R^{21}$ is $C_1$-$C_8$alkyl, benzyl or a group of the formula IV and $R^{22}$ is a group —O($C_1$-$C_4$alkyl) or a group of the formula V.

6. A colour photography recording material according to claim 3 in which n is 0 or 2, $R^1$ and $R^2$ are hydrogen or methyl, $R^3$ and $R^4$ are methyl, phenyl, thienyl or phenyl which is substituted by $C_1$-$C_4$alkyl, $C_1$-$C_4$alkoxy, hydroxyl or chlorine, $R^5$ and $R^6$ are hydrogen, $R^7$ is hydrogen or a group

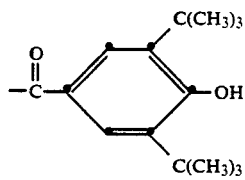

$R^8$ and $R^9$ independently of one another are hydrogen, $C_1$-$C_4$alkyl, cyclohexyl or phenyl, $R^{10}$ is hydrogen, T is one of the following trivalent groups:

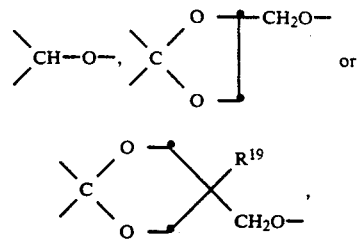

in which $R^{19}$ is $C_1$-$C_4$alkyl, and Z is one of the following divalent groups:

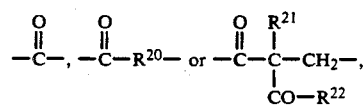

the carbonyl group of which is bonded to T and in which $R^{20}$ is $C_1$-$C_8$alkylene, $R^{21}$ is $C_1$-$C_8$alkyl, benzyl or a group of the formula IV and $R^{22}$ is —O($C_1$-$C_4$alkyl) or a group of the formula V.

7. A colour photography recording material according to claim 3 in which $R^1$, $R^2$, $R^5$ and $R^6$ are hydrogen.

8. A colour photography recording material according to claim 3 in which the compound is of formula I.

9. A colour photography recording material according to claim 3 in which the compound is of formula I or II, in which n is o.

10. A colour photography recording material according to claim 3 in which the compound is 3-[3-(3,5-di-tert-butyl-4-hydroxy-phenyl)-propionyloxymethyl]-3-ethyl-8,10-diphenyl-1,5-dioxa-9-thiaspiro-[5.5]undecane.

* * * * *